United States Patent
Nguyen et al.

(10) Patent No.: US 11,864,812 B2
(45) Date of Patent: Jan. 9, 2024

(54) ELECTROSURGICAL GENERATOR CONTROL SYSTEM

(71) Applicant: Applied Medical Resources Corporation, Rancho Santa Margarita, CA (US)

(72) Inventors: Michael Nguyen, Rancho Santa Margarita, CA (US); Igor Gorin, Rancho Santa Margarita, CA (US); Joanna Pang, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 906 days.

(21) Appl. No.: 16/562,362

(22) Filed: Sep. 5, 2019

(65) Prior Publication Data

US 2020/0069358 A1    Mar. 5, 2020

Related U.S. Application Data

(60) Provisional application No. 62/727,195, filed on Sep. 5, 2018.

(51) Int. Cl.
    *A61B 18/12*    (2006.01)
    *A61B 18/00*    (2006.01)
    *A61B 18/14*    (2006.01)

(52) U.S. Cl.
    CPC ...... *A61B 18/1206* (2013.01); *A61B 18/1445* (2013.01); *A61B 2018/0063* (2013.01);
    (Continued)

(58) Field of Classification Search
    CPC ............ A61B 18/1206; A61B 18/1445; A61B 2018/00601; A61B 2018/0063;
    (Continued)

(56) References Cited

U.S. PATENT DOCUMENTS

| 371,664 A | 10/1887 | Brannan et al. |
| 702,472 A | 6/1902 | Pignolet |

(Continued)

FOREIGN PATENT DOCUMENTS

| DE | 40 24 636 A1 | 2/1992 |
| DE | 40 24 636 C2 | 12/1992 |

(Continued)

OTHER PUBLICATIONS

International Preliminary Examining Authority/US, International Preliminary Report on Patentability for International Application No. PCT/US2019/059909, titled "Electro surgical System," dated May 27, 2021, 15 pgs.

(Continued)

*Primary Examiner* — Sean W Collins
(74) *Attorney, Agent, or Firm* — Shirin Bozorgui; Patrick Ikehara

(57) ABSTRACT

Systems and methods for enhancing surgical outcomes by providing generators having optimal RF output for sealing, fusing and/or cutting tissue or vessels under all dynamic conditions are described. Examples of dynamic conditions may include varying tissue impedance load due to electro-surgical operations or tissue affects, any operational conditions and commands determined by the surgeon, surgical procedure and/or device script. This is achieved by implementing a digital closed-loop control system within the electrosurgical generator to regulate voltage, current, and power of the RF output. The digital closed-loop control system may include an RF amplifier for generating RF energy, a feedback system for constantly monitoring the electrical characteristics, e.g., voltage, current, and power, of the supplied RF energy to a connectable electrosurgical instrument and a microcontroller for processing measurement data from the feedback system and adjusting the output (Continued)

of the RF amplifier to meet a desired regulation target under any varying conditions.

21 Claims, 9 Drawing Sheets

(52) U.S. Cl.
CPC ............... *A61B 2018/00601* (2013.01); *A61B 2018/00642* (2013.01); *A61B 2018/00726* (2013.01); *A61B 2018/00767* (2013.01); *A61B 2018/00779* (2013.01); *A61B 2018/00827* (2013.01); *A61B 2018/00875* (2013.01); *A61B 2018/00892* (2013.01); *H03F 2200/129* (2013.01); *H03F 2200/451* (2013.01); *H03G 2201/103* (2013.01); *H03G 2201/307* (2013.01)

(58) Field of Classification Search
CPC ........... A61B 2018/00642; A61B 2018/00726; A61B 2018/00779; A61B 2018/00827; A61B 2018/00875; A61B 2018/00892
See application file for complete search history.

(56) References Cited

U.S. PATENT DOCUMENTS

| | | | |
|---|---|---|---|
| 728,883 | A | 5/1903 | Downes |
| 1,586,645 | A | 6/1926 | Bierman |
| 1,935,289 | A | 11/1933 | Evans |
| 2,002,594 | A | 5/1935 | Wappler et al. |
| 2,031,682 | A | 2/1936 | Wappler et al. |
| 2,113,246 | A | 4/1938 | Wappler |
| 2,176,479 | A | 10/1939 | Willis |
| 2,305,156 | A | 12/1942 | Grubel |
| 2,632,661 | A | 3/1953 | Cristofv |
| 2,827,056 | A | 3/1958 | Degelman |
| 3,085,566 | A | 4/1963 | Tolles |
| 3,459,187 | A | 8/1969 | Pallotta |
| 3,494,363 | A | 2/1970 | Jackson |
| 3,588,710 | A | 6/1971 | Masters |
| 3,651,811 | A | 3/1972 | Hildebrandt et al. |
| 3,685,518 | A | 8/1972 | Beuerle et al. |
| 3,780,416 | A | 12/1973 | Rider |
| 3,826,263 | A | 7/1974 | Cage et al. |
| 3,911,766 | A | 10/1975 | Fridolph et al. |
| 3,920,021 | A | 11/1975 | Hiltebrandt |
| 3,938,527 | A | 2/1976 | Rioux et al. |
| 3,963,030 | A | 6/1976 | Newton |
| 3,970,088 | A | 7/1976 | Morrison |
| 3,980,085 | A | 9/1976 | Ikuno |
| 3,987,795 | A | 10/1976 | Morrison |
| 4,030,501 | A | 6/1977 | Archibald |
| 4,041,952 | A | 8/1977 | Morrison, Jr. et al. |
| 4,043,342 | A | 8/1977 | Morrison, Jr. |
| 4,060,088 | A | 11/1977 | Morrison, Jr. et al. |
| 4,074,718 | A | 2/1978 | Morrison, Jr. |
| 4,089,336 | A | 5/1978 | Cage et al. |
| 4,092,986 | A | 6/1978 | Schneiderman |
| 4,094,320 | A | 6/1978 | Newton et al. |
| 4,114,623 | A | 9/1978 | Meinke et al. |
| 4,126,137 | A | 11/1978 | Archibald |
| 4,154,240 | A | 5/1979 | Ikuno et al. |
| 4,171,700 | A | 10/1979 | Farin |
| 4,181,131 | A | 1/1980 | Ogui |
| 4,188,927 | A | 2/1980 | Harris |
| 4,196,734 | A | 4/1980 | Harris |
| 4,198,957 | A | 4/1980 | Cage et al. |
| 4,198,960 | A | 4/1980 | Utsugi |
| 4,200,104 | A | 4/1980 | Harris |
| 4,231,372 | A | 11/1980 | Newton |
| 4,237,887 | A | 12/1980 | Gonser |
| 4,244,371 | A | 1/1981 | Farin |
| 4,325,374 | A | 4/1982 | Komiya |
| 4,331,149 | A | 5/1982 | Gonser |
| 4,338,940 | A | 7/1982 | Ikuno |
| 4,352,156 | A | 9/1982 | Gyugyi |
| 4,370,980 | A | 2/1983 | Lottick |
| 4,416,276 | A | 11/1983 | Newton et al. |
| 4,416,277 | A | 11/1983 | Newton et al. |
| 4,427,014 | A | 1/1984 | Bel et al. |
| 4,429,694 | A | 2/1984 | McGreevy |
| 4,463,759 | A | 8/1984 | Garito et al. |
| 4,487,489 | A | 12/1984 | Takamatsu |
| 4,514,619 | A | 4/1985 | Kugelman |
| 4,522,206 | A | 6/1985 | Whipple et al. |
| 4,552,143 | A | 11/1985 | Lottick |
| 4,569,131 | A | 2/1986 | Faulk et al. |
| 4,569,345 | A | 2/1986 | Manes |
| 4,590,934 | A | 5/1986 | Malis et al. |
| 4,599,553 | A | 7/1986 | Brennen et al. |
| 4,630,218 | A | 12/1986 | Hurley |
| 4,632,109 | A | 12/1986 | Paterson |
| 4,644,950 | A | 2/1987 | Valli |
| 4,651,280 | A | 3/1987 | Chang et al. |
| 4,655,216 | A | 4/1987 | Tischer |
| 4,657,018 | A | 4/1987 | Hakky |
| 4,658,815 | A | 4/1987 | Farin et al. |
| 4,658,819 | A | 4/1987 | Harris et al. |
| 4,658,820 | A | 4/1987 | Klicek |
| 4,674,498 | A | 6/1987 | Stasz |
| 4,685,459 | A | 8/1987 | Koch et al. |
| 4,699,146 | A | 10/1987 | Sieverding |
| 4,712,545 | A | 12/1987 | Honkanen |
| 4,716,897 | A | 1/1988 | Noguchi et al. |
| 4,727,874 | A | 3/1988 | Bowers et al. |
| 4,739,759 | A | 4/1988 | Rexroth et al. |
| 4,741,334 | A | 5/1988 | Irnich |
| 4,752,864 | A | 6/1988 | Clappier |
| 4,754,757 | A | 7/1988 | Feucht |
| 4,788,977 | A | 12/1988 | Farin et al. |
| 4,802,476 | A | 2/1989 | Noerenberg et al. |
| 4,818,954 | A | 4/1989 | Flachenecker et al. |
| 4,827,927 | A | 5/1989 | Newton |
| 4,848,335 | A | 7/1989 | Manes |
| 4,850,353 | A | 7/1989 | Stasz et al. |
| 4,860,745 | A | 8/1989 | Farin et al. |
| 4,862,889 | A | 9/1989 | Feucht |
| 4,862,890 | A | 9/1989 | Stasz et al. |
| 4,872,456 | A | 10/1989 | Hasson |
| 4,887,612 | A | 12/1989 | Esser et al. |
| 4,889,722 | A | 12/1989 | Sheffield et al. |
| 4,903,696 | A | 2/1990 | Stasz et al. |
| 4,905,691 | A | 3/1990 | Rydell |
| 4,922,903 | A | 5/1990 | Welch et al. |
| 4,936,281 | A | 6/1990 | Stasz |
| 4,937,254 | A | 6/1990 | Sheffield et al. |
| 4,938,761 | A | 7/1990 | Ensslin |
| 4,942,313 | A | 7/1990 | Kinzel |
| 4,958,539 | A | 9/1990 | Stasz et al. |
| 4,969,885 | A | 11/1990 | Farin |
| 4,976,711 | A | 12/1990 | Parins et al. |
| 5,007,908 | A | 4/1991 | Rydell |
| 5,013,312 | A | 5/1991 | Parins et al. |
| 5,015,227 | A | 5/1991 | Broadwin et al. |
| 5,016,521 | A | 5/1991 | Haka |
| 5,026,370 | A | 6/1991 | Lottick |
| 5,026,371 | A | 6/1991 | Rydell et al. |
| 5,035,696 | A | 7/1991 | Rydell |
| 5,038,109 | A | 8/1991 | Goble et al. |
| 5,047,026 | A | 9/1991 | Rydell |
| 5,047,027 | A | 9/1991 | Rydell |
| 5,052,402 | A | 10/1991 | Bencini et al. |
| 5,057,107 | A | 10/1991 | Parins et al. |
| 5,061,269 | A | 10/1991 | Muller |
| 5,062,031 | A | 10/1991 | Flachenecker et al. |
| 5,071,419 | A | 12/1991 | Rydell et al. |
| 5,078,717 | A | 1/1992 | Parins et al. |
| 5,083,565 | A | 1/1992 | Parins |
| 5,085,659 | A | 2/1992 | Rydell |
| 5,087,257 | A | 2/1992 | Farin et al. |
| 5,098,431 | A | 3/1992 | Rydell |
| 5,116,332 | A | 5/1992 | Lottick |

(56) References Cited

U.S. PATENT DOCUMENTS

| | | |
|---|---|---|
| 5,122,137 A | 6/1992 | Lennox |
| 5,125,928 A | 6/1992 | Parins et al. |
| 5,127,412 A | 7/1992 | Cosmetto et al. |
| 5,151,102 A | 9/1992 | Kamiyama et al. |
| 5,158,561 A | 10/1992 | Rydell et al. |
| 5,160,343 A | 11/1992 | Brancel et al. |
| 5,167,658 A | 12/1992 | Ensslin |
| 5,171,255 A | 12/1992 | Rydell |
| 5,171,311 A | 12/1992 | Rydell |
| 5,190,517 A | 3/1993 | Zieve et al. |
| 5,190,541 A | 3/1993 | Abele et al. |
| 5,192,280 A | 3/1993 | Parins |
| 5,197,963 A | 3/1993 | Parins |
| 5,197,964 A | 3/1993 | Parins |
| 5,201,732 A | 4/1993 | Parins et al. |
| 5,217,457 A | 6/1993 | Delahuerga et al. |
| 5,217,458 A | 6/1993 | Parins |
| 5,234,427 A | 8/1993 | Ohtomo et al. |
| 5,244,462 A | 9/1993 | Delahuerga et al. |
| 5,246,440 A | 9/1993 | Van Noord |
| 5,250,047 A | 10/1993 | Rydell |
| 5,250,056 A | 10/1993 | Hasson |
| 5,254,126 A | 10/1993 | Filipi et al. |
| 5,256,149 A | 10/1993 | Banik et al. |
| 5,258,006 A | 11/1993 | Rydell et al. |
| 5,267,997 A | 12/1993 | Farin et al. |
| 5,269,780 A | 12/1993 | Roos |
| 5,273,524 A | 12/1993 | Fox et al. |
| 5,281,216 A | 1/1994 | Klicek |
| 5,282,799 A | 2/1994 | Rydell |
| 5,286,255 A | 2/1994 | Weber |
| 5,290,286 A | 3/1994 | Parins |
| 5,300,070 A | 4/1994 | Gentelia et al. |
| 5,304,190 A | 4/1994 | Reckelhoff et al. |
| 5,312,329 A | 5/1994 | Beaty et al. |
| 5,314,424 A | 5/1994 | Nicholas |
| 5,318,563 A | 6/1994 | Malis et al. |
| 5,322,055 A | 6/1994 | Davison et al. |
| 5,324,289 A | 6/1994 | Eggers |
| 5,330,471 A | 7/1994 | Eggers |
| 5,334,183 A | 8/1994 | Wuchinich |
| 5,338,317 A | 8/1994 | Hasson et al. |
| 5,341,807 A | 8/1994 | Nardella |
| 5,341,815 A | 8/1994 | Cofone et al. |
| 5,342,359 A | 8/1994 | Rydell |
| 5,342,381 A | 8/1994 | Tidemand |
| 5,352,222 A | 10/1994 | Rydell |
| 5,352,223 A | 10/1994 | McBrayer et al. |
| 5,354,313 A | 10/1994 | Boebel |
| 5,356,408 A | 10/1994 | Rydell |
| 5,370,645 A | 12/1994 | Klicek et al. |
| 5,372,124 A | 12/1994 | Takayama et al. |
| 5,372,596 A | 12/1994 | Klicek et al. |
| 5,374,277 A | 12/1994 | Hassler |
| 5,382,247 A | 1/1995 | Cimino et al. |
| 5,383,880 A | 1/1995 | Hooven |
| 5,383,922 A | 1/1995 | Zipes et al. |
| 5,387,196 A | 2/1995 | Green et al. |
| 5,387,197 A | 2/1995 | Smith et al. |
| 5,389,104 A | 2/1995 | Hahnen et al. |
| 5,389,849 A | 2/1995 | Asano et al. |
| 5,391,166 A | 2/1995 | Eggers |
| 5,392,917 A | 2/1995 | Alpern et al. |
| 5,400,267 A | 3/1995 | Denen et al. |
| 5,403,312 A | 4/1995 | Yates et al. |
| 5,403,342 A | 4/1995 | Tovey et al. |
| 5,405,344 A | 4/1995 | Willaimson et al. |
| 5,409,498 A | 4/1995 | Braddock et al. |
| 5,417,687 A | 5/1995 | Nardella et al. |
| 5,422,567 A | 6/1995 | Matsunaga |
| 5,423,808 A | 6/1995 | Edwards et al. |
| 5,423,810 A | 6/1995 | Goble et al. |
| 5,431,638 A | 7/1995 | Hennig et al. |
| 5,431,649 A | 7/1995 | Mulier et al. |
| 5,431,674 A | 7/1995 | Basile et al. |
| 5,432,459 A | 7/1995 | Thompson et al. |
| 5,436,566 A | 7/1995 | Thompson et al. |
| 5,437,664 A | 8/1995 | Cohen et al. |
| 5,438,302 A | 8/1995 | Goble |
| 5,443,463 A | 8/1995 | Stern et al. |
| 5,445,142 A | 8/1995 | Hassler, Jr. |
| 5,445,638 A | 8/1995 | Rydell et al. |
| 5,447,513 A | 9/1995 | Davison et al. |
| 5,449,355 A | 9/1995 | Rhum et al. |
| 5,456,684 A | 10/1995 | Schmidt et al. |
| 5,458,598 A | 10/1995 | Feinberg et al. |
| 5,460,182 A | 10/1995 | Goodman et al. |
| 5,462,546 A | 10/1995 | Rydell |
| 5,464,144 A | 11/1995 | Guy et al. |
| 5,472,439 A | 12/1995 | Hurd |
| 5,472,442 A | 12/1995 | Klicek |
| 5,472,443 A | 12/1995 | Cordis et al. |
| 5,472,451 A | 12/1995 | Freitas et al. |
| 5,474,057 A | 12/1995 | Makower et al. |
| 5,476,479 A | 12/1995 | Green et al. |
| 5,478,351 A | 12/1995 | Meade et al. |
| 5,484,400 A | 1/1996 | Edwards et al. |
| 5,486,185 A | 1/1996 | Freitas et al. |
| 5,496,312 A | 3/1996 | Klicek |
| 5,496,317 A | 3/1996 | Goble et al. |
| 5,499,992 A | 3/1996 | Meade et al. |
| 5,499,998 A | 3/1996 | Meade et al. |
| 5,503,320 A | 4/1996 | Webster et al. |
| 5,507,773 A | 4/1996 | Huitema et al. |
| 5,509,916 A | 4/1996 | Taylor |
| 5,514,129 A | 5/1996 | Smith |
| 5,514,134 A | 5/1996 | Rydell et al. |
| 5,518,163 A | 5/1996 | Hooven |
| 5,518,164 A | 5/1996 | Hooven |
| 5,527,313 A | 6/1996 | Scott et al. |
| 5,527,330 A | 6/1996 | Tovey |
| 5,531,744 A | 7/1996 | Nardella et al. |
| 5,540,681 A | 7/1996 | Strul et al. |
| 5,540,684 A | 7/1996 | Hassler, Jr. |
| 5,540,685 A | 7/1996 | Parins et al. |
| 5,541,376 A | 7/1996 | Ladtkow et al. |
| 5,551,945 A | 9/1996 | Yabe et al. |
| 5,558,429 A | 9/1996 | Cain |
| 5,558,671 A | 9/1996 | Yates |
| 5,562,699 A | 10/1996 | Heimberger et al. |
| 5,562,700 A | 10/1996 | Huitema et al. |
| 5,571,100 A | 11/1996 | Goble et al. |
| 5,571,121 A | 11/1996 | Heifetz |
| 5,573,424 A | 11/1996 | Poppe |
| 5,573,533 A | 11/1996 | Strul |
| 5,573,534 A | 11/1996 | Stone |
| 5,573,535 A | 11/1996 | Viklund |
| 5,575,789 A | 11/1996 | Bell et al. |
| 5,575,805 A | 11/1996 | Li |
| 5,584,830 A | 12/1996 | Ladd et al. |
| 5,599,344 A | 2/1997 | Paterson |
| 5,599,350 A | 2/1997 | Schulze et al. |
| 5,603,711 A | 2/1997 | Parins et al. |
| D378,611 S | 3/1997 | Croley |
| 5,607,391 A | 3/1997 | Klinger et al. |
| 5,609,151 A | 3/1997 | Mulier et al. |
| 5,609,560 A | 3/1997 | Ichikawa et al. |
| 5,609,573 A | 3/1997 | Sandock |
| 5,611,709 A | 3/1997 | McAnulty |
| 5,613,966 A | 3/1997 | Makower et al. |
| 5,620,415 A | 4/1997 | Lucey et al. |
| 5,620,447 A | 4/1997 | Smith et al. |
| 5,624,452 A | 4/1997 | Yates |
| 5,626,575 A | 5/1997 | Crenner |
| 5,626,607 A | 5/1997 | Malecki et al. |
| 5,626,608 A | 5/1997 | Cuny et al. |
| 5,627,584 A | 5/1997 | Nishikori et al. |
| 5,633,578 A | 5/1997 | Eggers et al. |
| 5,645,540 A | 7/1997 | Henniges et al. |
| 5,647,869 A | 7/1997 | Goble et al. |
| 5,651,780 A | 7/1997 | Jackson et al. |
| 5,658,279 A | 8/1997 | Nardella et al. |
| 5,658,281 A | 8/1997 | Heard |
| 5,665,100 A | 9/1997 | Yoon |

(56) References Cited

U.S. PATENT DOCUMENTS

| | | |
|---|---|---|
| 5,665,105 A | 9/1997 | Furnish et al. |
| 5,667,517 A | 9/1997 | Hooven |
| 5,669,907 A | 9/1997 | Platt, Jr. et al. |
| 5,674,184 A | 10/1997 | Hassler, Jr. |
| 5,674,220 A | 10/1997 | Fox et al. |
| 5,683,349 A | 11/1997 | Makower et al. |
| 5,688,270 A | 11/1997 | Yates et al. |
| 5,693,045 A | 12/1997 | Eggers |
| 5,693,051 A | 12/1997 | Schulze et al. |
| 5,695,494 A | 12/1997 | Becker |
| 5,697,281 A | 12/1997 | Eggers et al. |
| 5,697,909 A | 12/1997 | Eggers et al. |
| 5,700,261 A | 12/1997 | Brinkerhoff |
| 5,702,386 A | 12/1997 | Stern et al. |
| 5,702,387 A | 12/1997 | Arts et al. |
| 5,702,390 A | 12/1997 | Austin et al. |
| 5,707,369 A | 1/1998 | Vaitekunas et al. |
| 5,709,680 A | 1/1998 | Yates et al. |
| 5,713,128 A | 2/1998 | Schrenk et al. |
| 5,713,895 A | 2/1998 | Lontine et al. |
| 5,713,896 A | 2/1998 | Nardella |
| 5,720,742 A | 2/1998 | Quinn et al. |
| 5,720,744 A | 2/1998 | Eggleston et al. |
| 5,720,745 A | 2/1998 | Farin et al. |
| 5,722,975 A | 3/1998 | Edwards et al. |
| 5,725,524 A | 3/1998 | Mulier et al. |
| 5,735,848 A | 4/1998 | Yates et al. |
| 5,735,849 A | 4/1998 | Baden et al. |
| 5,743,456 A | 4/1998 | Jones et al. |
| 5,743,906 A | 4/1998 | Parins et al. |
| 5,746,210 A | 5/1998 | Benaron et al. |
| 5,746,740 A | 5/1998 | Nicholas |
| 5,746,759 A | 5/1998 | Meade et al. |
| 5,752,519 A | 5/1998 | Benaron et al. |
| 5,755,717 A | 5/1998 | Yates et al. |
| 5,759,185 A | 6/1998 | Grinberg |
| 5,762,609 A | 6/1998 | Benaron et al. |
| 5,766,167 A | 6/1998 | Eggers et al. |
| 5,769,791 A | 6/1998 | Benaron et al. |
| 5,769,841 A | 6/1998 | Odell et al. |
| 5,772,597 A | 6/1998 | Goldberger et al. |
| 5,772,659 A | 6/1998 | Becker et al. |
| 5,772,660 A | 6/1998 | Young et al. |
| 5,776,092 A | 7/1998 | Farin et al. |
| 5,776,129 A | 7/1998 | Mersch |
| 5,776,130 A | 7/1998 | Buysse et al. |
| 5,776,155 A | 7/1998 | Beaupre et al. |
| 5,782,397 A | 7/1998 | Koukline |
| 5,785,658 A | 7/1998 | Benaron et al. |
| 5,792,139 A | 8/1998 | Chambers et al. |
| 5,792,178 A | 8/1998 | Welch et al. |
| 5,797,906 A | 8/1998 | Rhum et al. |
| 5,797,938 A | 8/1998 | Paraschac et al. |
| 5,797,941 A | 8/1998 | Schulze et al. |
| 5,800,449 A | 9/1998 | Wales |
| 5,807,261 A | 9/1998 | Benaron et al. |
| 5,807,393 A | 9/1998 | Williamson, IV et al. |
| 5,807,395 A | 9/1998 | Mulier et al. |
| 5,810,806 A | 9/1998 | Ritchart et al. |
| 5,810,811 A | 9/1998 | Yates et al. |
| 5,810,859 A | 9/1998 | DiMatteo et al. |
| 5,817,091 A | 10/1998 | Nardella et al. |
| 5,817,093 A | 10/1998 | Williamson, IV et al. |
| 5,817,119 A | 10/1998 | Klieman et al. |
| 5,827,271 A | 10/1998 | Buysse et al. |
| 5,827,279 A | 10/1998 | Hughett et al. |
| 5,827,299 A | 10/1998 | Thomason et al. |
| 5,830,231 A | 11/1998 | Geiges, Jr. |
| 5,833,690 A | 11/1998 | Yates et al. |
| 5,836,942 A | 11/1998 | Netherly et al. |
| 5,836,943 A | 11/1998 | Miller, III |
| 5,846,194 A | 12/1998 | Wasson et al. |
| 5,849,020 A | 12/1998 | Long et al. |
| 5,853,412 A | 12/1998 | Mayenberger |
| 5,860,975 A | 1/1999 | Goble et al. |
| 5,873,873 A | 2/1999 | Smith et al. |
| 5,876,398 A | 3/1999 | Mulier et al. |
| 5,876,401 A | 3/1999 | Schulze et al. |
| 5,885,277 A | 3/1999 | Korth |
| 5,891,095 A | 4/1999 | Eggers et al. |
| 5,891,141 A | 4/1999 | Rydell |
| 5,891,142 A | 4/1999 | Eggers et al. |
| 5,893,835 A | 4/1999 | Witt et al. |
| 5,893,873 A | 4/1999 | Rader et al. |
| 5,897,490 A | 4/1999 | Fox et al. |
| 5,897,523 A | 4/1999 | Wright et al. |
| 5,897,553 A | 4/1999 | Mulier et al. |
| 5,897,569 A | 4/1999 | Kellogg et al. |
| 5,902,264 A | 5/1999 | Toso et al. |
| 5,902,301 A | 5/1999 | Olig |
| 5,904,709 A | 5/1999 | Arndt et al. |
| 5,906,613 A | 5/1999 | Mulier et al. |
| 5,908,402 A | 6/1999 | Blythe |
| 5,908,420 A | 6/1999 | Parins et al. |
| 5,910,152 A | 6/1999 | Bays |
| 5,928,137 A | 7/1999 | Green |
| 5,928,255 A | 7/1999 | Meade et al. |
| 5,928,256 A | 7/1999 | Riza |
| 5,931,836 A | 8/1999 | Hatta et al. |
| 5,935,126 A | 8/1999 | Riza |
| 5,938,633 A | 8/1999 | Beaupre |
| 5,944,715 A | 8/1999 | Goble et al. |
| 5,944,718 A | 8/1999 | Austin et al. |
| 5,944,737 A | 8/1999 | Tsonton et al. |
| 5,947,284 A | 9/1999 | Foster |
| 5,947,984 A | 9/1999 | Whipple |
| 5,951,552 A | 9/1999 | Long et al. |
| 5,954,736 A | 9/1999 | Bishop et al. |
| 5,954,746 A | 9/1999 | Holthaus et al. |
| 5,957,943 A | 9/1999 | Vaitekunas |
| 5,961,514 A | 10/1999 | Long et al. |
| 5,968,062 A | 10/1999 | Thomas et al. |
| 5,968,074 A | 10/1999 | Prestel |
| 5,976,077 A | 11/1999 | Wittens et al. |
| 5,976,128 A | 11/1999 | Schilling et al. |
| 5,980,510 A | 11/1999 | Tsonton et al. |
| 5,980,516 A | 11/1999 | Mulier et al. |
| 5,984,921 A | 11/1999 | Long et al. |
| 5,987,346 A | 11/1999 | Benaron et al. |
| 5,993,380 A | 11/1999 | Yabe et al. |
| 5,993,447 A | 11/1999 | Blewett et al. |
| 5,995,875 A | 11/1999 | Blewett et al. |
| 5,997,533 A | 12/1999 | Kuhns |
| 6,003,517 A | 12/1999 | Sheffield et al. |
| 6,004,319 A | 12/1999 | Goble et al. |
| 6,004,335 A | 12/1999 | Vaitekunas et al. |
| 6,010,499 A | 1/2000 | Cobb |
| 6,010,516 A | 1/2000 | Hulka |
| 6,013,076 A | 1/2000 | Goble et al. |
| 6,015,406 A | 1/2000 | Goble et al. |
| 6,016,809 A | 1/2000 | Mulier et al. |
| D420,741 S | 2/2000 | Croley |
| 6,024,741 A | 2/2000 | Williamson, IV et al. |
| 6,024,744 A | 2/2000 | Kese et al. |
| 6,027,501 A | 2/2000 | Goble et al. |
| 6,027,522 A | 2/2000 | Palmer |
| 6,030,384 A | 2/2000 | Nezhat |
| 6,030,402 A | 2/2000 | Thompson et al. |
| 6,033,399 A | 3/2000 | Gines |
| 6,033,404 A | 3/2000 | Melzer et al. |
| 6,036,657 A | 3/2000 | Milliman et al. |
| 6,039,733 A | 3/2000 | Buysse et al. |
| 6,039,734 A | 3/2000 | Goble |
| 6,039,736 A | 3/2000 | Platt, Jr. |
| 6,050,996 A | 4/2000 | Schmaltz et al. |
| 6,051,010 A | 4/2000 | DiMatteo et al. |
| 6,053,172 A | 4/2000 | Hovda et al. |
| 6,053,914 A | 4/2000 | Eggers et al. |
| 6,056,746 A | 5/2000 | Goble et al. |
| 6,063,050 A | 5/2000 | Manna et al. |
| 6,063,075 A | 5/2000 | Mihori |
| 6,063,081 A | 5/2000 | Mulier et al. |
| 6,063,086 A | 5/2000 | Benecke et al. |
| 6,066,139 A | 5/2000 | Ryan et al. |

(56) References Cited

U.S. PATENT DOCUMENTS

| | | |
|---|---|---|
| 6,068,627 A | 5/2000 | Orszulak et al. |
| 6,068,647 A | 5/2000 | Witt et al. |
| 6,070,444 A | 6/2000 | Lontine et al. |
| 6,074,386 A | 6/2000 | Goble et al. |
| RE36,795 E | 7/2000 | Rydell |
| 6,083,191 A | 7/2000 | Rose |
| 6,086,586 A | 7/2000 | Hooven |
| 6,090,106 A | 7/2000 | Goble et al. |
| 6,090,120 A | 7/2000 | Wright et al. |
| 6,092,722 A | 7/2000 | Heinrichs et al. |
| 6,093,186 A | 7/2000 | Goble |
| 6,096,037 A | 8/2000 | Mulier et al. |
| 6,102,909 A | 8/2000 | Chen et al. |
| 6,106,521 A | 8/2000 | Blewett et al. |
| 6,109,268 A | 8/2000 | Thapliyal et al. |
| 6,110,171 A | 8/2000 | Rydell |
| 6,113,591 A | 9/2000 | Whayne et al. |
| 6,113,594 A | 9/2000 | Savage |
| 6,113,596 A | 9/2000 | Hooven et al. |
| 6,113,598 A | 9/2000 | Baker |
| 6,117,152 A | 9/2000 | Huitema |
| 6,120,501 A | 9/2000 | Long et al. |
| H1904 H | 10/2000 | Yates |
| 6,132,429 A | 10/2000 | Baker |
| 6,135,998 A | 10/2000 | Palanker |
| 6,139,519 A | 10/2000 | Blythe |
| 6,139,547 A | 10/2000 | Lontine et al. |
| 6,142,992 A | 11/2000 | Cheng et al. |
| 6,152,923 A | 11/2000 | Ryan |
| 6,159,146 A | 12/2000 | El Gazayerli |
| 6,162,235 A | 12/2000 | Vaitekunas |
| 6,165,175 A | 12/2000 | Wampler et al. |
| 6,168,605 B1 | 1/2001 | Measamer et al. |
| 6,171,304 B1 | 1/2001 | Netherly et al. |
| 6,174,308 B1 | 1/2001 | Goble et al. |
| 6,174,309 B1 | 1/2001 | Wroblewski et al. |
| 6,179,834 B1 | 1/2001 | Buysse et al. |
| 6,186,147 B1 | 2/2001 | Cobb |
| 6,187,003 B1 | 2/2001 | Buysse et al. |
| 6,187,026 B1 | 2/2001 | Devlin et al. |
| 6,190,383 B1 | 2/2001 | Schmaltz et al. |
| 6,190,385 B1 | 2/2001 | Tom et al. |
| 6,190,386 B1 | 2/2001 | Rydell |
| 6,193,129 B1 | 2/2001 | Bittner et al. |
| 6,193,653 B1 | 2/2001 | Evans et al. |
| 6,193,713 B1 | 2/2001 | Geistert et al. |
| 6,197,026 B1 | 3/2001 | Farin et al. |
| 6,203,541 B1 | 3/2001 | Keppel |
| 6,206,823 B1 | 3/2001 | Kolata et al. |
| 6,206,844 B1 | 3/2001 | Reichel et al. |
| 6,206,875 B1 | 3/2001 | Long et al. |
| 6,206,877 B1 | 3/2001 | Kese et al. |
| 6,210,403 B1 | 4/2001 | Klicek |
| 6,210,405 B1 | 4/2001 | Goble et al. |
| 6,214,003 B1 | 4/2001 | Morgan et al. |
| 6,214,023 B1 | 4/2001 | Whipple et al. |
| 6,228,023 B1 | 5/2001 | Zaslavsky et al. |
| 6,228,055 B1 | 5/2001 | Foerster et al. |
| 6,228,080 B1 | 5/2001 | Gines |
| 6,228,081 B1 | 5/2001 | Goble |
| 6,228,083 B1 | 5/2001 | Lands et al. |
| 6,234,178 B1 | 5/2001 | Goble et al. |
| 6,237,604 B1 | 5/2001 | Burnside et al. |
| 6,238,366 B1 | 5/2001 | Savage et al. |
| 6,238,392 B1 | 5/2001 | Long |
| 6,238,393 B1 | 5/2001 | Mulier et al. |
| 6,242,741 B1 | 6/2001 | Miller et al. |
| 6,246,912 B1 | 6/2001 | Sluijter et al. |
| 6,251,106 B1 | 6/2001 | Becker et al. |
| 6,251,110 B1 | 6/2001 | Wampler |
| 6,254,623 B1 | 7/2001 | Haibel, Jr. et al. |
| 6,257,241 B1 | 7/2001 | Wampler |
| 6,258,085 B1 | 7/2001 | Eggleston |
| 6,261,286 B1 | 7/2001 | Goble et al. |
| 6,267,761 B1 | 7/2001 | Ryan |
| 6,270,497 B1 | 8/2001 | Sekino et al. |
| 6,273,862 B1 | 8/2001 | Privitera et al. |
| 6,277,114 B1 | 8/2001 | Bullivant et al. |
| 6,277,115 B1 | 8/2001 | Saadat |
| 6,277,117 B1 | 8/2001 | Tetzlaff et al. |
| 6,280,398 B1 | 8/2001 | Ritchart et al. |
| 6,280,407 B1 | 8/2001 | Manna et al. |
| 6,280,441 B1 | 8/2001 | Ryan |
| 6,283,963 B1 | 9/2001 | Regula |
| 6,287,344 B1 | 9/2001 | Wampler |
| 6,293,942 B1 | 9/2001 | Goble et al. |
| 6,293,945 B1 | 9/2001 | Parins et al. |
| 6,296,637 B1 | 10/2001 | Thorne et al. |
| 6,296,640 B1 | 10/2001 | Wampler et al. |
| 6,298,550 B1 | 10/2001 | Kirwan, Jr. |
| 6,302,903 B1 | 10/2001 | Mulier et al. |
| 6,306,131 B1 | 10/2001 | Hareyama et al. |
| 6,306,134 B1 | 10/2001 | Goble et al. |
| 6,308,089 B1 | 10/2001 | von der Ruhr et al. |
| 6,309,400 B2 | 10/2001 | Beaupre |
| 6,312,426 B1 | 11/2001 | Goldberg et al. |
| 6,315,777 B1 | 11/2001 | Comben |
| 6,319,221 B1 | 11/2001 | Savage et al. |
| 6,322,494 B1 | 11/2001 | Bullivant et al. |
| 6,322,549 B1 | 11/2001 | Eggers et al. |
| 6,322,561 B1 | 11/2001 | Eggers et al. |
| 6,325,795 B1 | 12/2001 | Lindemann et al. |
| 6,325,799 B1 | 12/2001 | Goble |
| 6,325,811 B1 | 12/2001 | Messerly |
| 6,328,736 B1 | 12/2001 | Mulier et al. |
| 6,328,751 B1 | 12/2001 | Beaupre |
| 6,331,181 B1 | 12/2001 | Tierney et al. |
| 6,334,068 B1 | 12/2001 | Hacker |
| 6,334,861 B1 | 1/2002 | Chandler et al. |
| 6,336,926 B1 | 1/2002 | Goble |
| 6,348,051 B1 | 2/2002 | Farin et al. |
| 6,352,532 B1 | 3/2002 | Kramer et al. |
| 6,352,536 B1 | 3/2002 | Buysse et al. |
| 6,358,248 B1 | 3/2002 | Mulier et al. |
| 6,358,249 B1 | 3/2002 | Chen et al. |
| 6,358,267 B1 | 3/2002 | Murakami |
| 6,361,534 B1 | 3/2002 | Chen et al. |
| 6,364,877 B1 | 4/2002 | Goble et al. |
| 6,364,879 B1 | 4/2002 | Chen et al. |
| 6,371,967 B1 | 4/2002 | Long et al. |
| D457,958 S | 5/2002 | Dycus et al. |
| 6,383,183 B1 | 5/2002 | Sekino et al. |
| 6,387,092 B1 | 5/2002 | Burnside et al. |
| 6,387,109 B1 | 5/2002 | Davison et al. |
| 6,391,024 B1 | 5/2002 | Sun et al. |
| 6,391,025 B1 | 5/2002 | Weinstein et al. |
| 6,398,779 B1 | 6/2002 | Buysse et al. |
| 6,398,781 B1 | 6/2002 | Goble et al. |
| 6,402,741 B1 | 6/2002 | Keppel et al. |
| 6,402,742 B1 | 6/2002 | Blewett et al. |
| 6,402,743 B1 | 6/2002 | Orszulak et al. |
| 6,402,747 B1 | 6/2002 | Lindemann et al. |
| 6,402,748 B1 | 6/2002 | Schoenman et al. |
| 6,406,475 B1 | 6/2002 | Wenzler et al. |
| 6,409,722 B1 | 6/2002 | Hoey et al. |
| 6,409,724 B1 | 6/2002 | Penny et al. |
| 6,409,728 B1 | 6/2002 | Ehr et al. |
| 6,416,486 B1 | 7/2002 | Wampler |
| 6,416,509 B1 | 7/2002 | Goble et al. |
| 6,423,057 B1 | 7/2002 | He et al. |
| 6,423,082 B1 | 7/2002 | Houser et al. |
| 6,432,118 B1 | 8/2002 | Messerly |
| 6,436,096 B1 | 8/2002 | Hareyama |
| 6,440,130 B1 | 8/2002 | Mulier et al. |
| 6,443,952 B1 | 9/2002 | Mulier et al. |
| 6,443,968 B1 | 9/2002 | Holthaus et al. |
| 6,443,970 B1 | 9/2002 | Schulze et al. |
| 6,451,013 B1 | 9/2002 | Bays et al. |
| 6,451,018 B1 | 9/2002 | Lands et al. |
| 6,454,764 B1 | 9/2002 | Fleenor et al. |
| 6,454,781 B1 | 9/2002 | Witt et al. |
| 6,454,782 B1 | 9/2002 | Schwemberger |
| 6,458,078 B1 | 10/2002 | Lüdtke et al. |
| 6,458,128 B1 | 10/2002 | Schulze |

(56) References Cited

U.S. PATENT DOCUMENTS

| | | |
|---|---|---|
| 6,458,130 B1 | 10/2002 | Frazier et al. |
| 6,458,142 B1 | 10/2002 | Faller et al. |
| 6,461,352 B2 | 10/2002 | Morgan et al. |
| 6,464,689 B1 | 10/2002 | Qin et al. |
| 6,464,702 B2 | 10/2002 | Schulze et al. |
| 6,464,704 B2 | 10/2002 | Schmaltz et al. |
| 6,468,275 B1 | 10/2002 | Wampler et al. |
| 6,468,286 B2 | 10/2002 | Mastri et al. |
| 6,475,217 B1 | 11/2002 | Platt |
| 6,478,030 B1 | 11/2002 | Shapeton et al. |
| 6,482,202 B1 | 11/2002 | Goble et al. |
| 6,485,490 B2 | 11/2002 | Wampler et al. |
| 6,488,507 B1 | 12/2002 | Stoloff et al. |
| 6,488,680 B1 | 12/2002 | Francischelli et al. |
| 6,491,690 B1 | 12/2002 | Goble et al. |
| 6,491,708 B2 | 12/2002 | Madan et al. |
| 6,493,589 B1 | 12/2002 | Medhkour et al. |
| 6,494,877 B2 | 12/2002 | Odell et al. |
| 6,494,902 B2 | 12/2002 | Hoey et al. |
| 6,497,705 B2 | 12/2002 | Comben |
| 6,500,176 B1 | 12/2002 | Truckai et al. |
| 6,500,188 B2 | 12/2002 | Harper et al. |
| 6,503,263 B2 | 1/2003 | Adams |
| 6,506,189 B1 | 1/2003 | Rittman, III et al. |
| 6,506,208 B2 | 1/2003 | Hunt et al. |
| 6,510,854 B2 | 1/2003 | Goble et al. |
| 6,511,476 B2 | 1/2003 | Hareyama |
| 6,511,480 B1 | 1/2003 | Tetzlaff et al. |
| 6,514,252 B2 | 2/2003 | Nezhat et al. |
| 6,517,536 B2 | 2/2003 | Hooven et al. |
| 6,517,538 B1 | 2/2003 | Jacob et al. |
| 6,526,320 B2 | 2/2003 | Mitchell |
| 6,527,771 B1 | 3/2003 | Weadock et al. |
| 6,533,784 B2 | 3/2003 | Truckai et al. |
| 6,534,770 B2 | 3/2003 | Miller et al. |
| 6,537,248 B2 | 3/2003 | Mulier et al. |
| 6,537,272 B2 | 3/2003 | Christopherson et al. |
| 6,540,695 B1 | 4/2003 | Burbank et al. |
| 6,543,456 B1 | 4/2003 | Freeman |
| 6,547,783 B1 | 4/2003 | Vilendrer et al. |
| 6,547,786 B1 | 4/2003 | Goble et al. |
| 6,554,829 B2 | 4/2003 | Schulze et al. |
| 6,558,379 B1 | 5/2003 | Batchelor et al. |
| 6,558,383 B2 | 5/2003 | Cunningham et al. |
| 6,561,983 B2 | 5/2003 | Cronin et al. |
| 6,562,037 B2 | 5/2003 | Paton et al. |
| 6,565,559 B2 | 5/2003 | Eggleston |
| 6,565,560 B1 | 5/2003 | Goble et al. |
| 6,569,105 B1 | 5/2003 | Kortenbach et al. |
| 6,569,109 B2 | 5/2003 | Sakurai et al. |
| 6,572,615 B2 | 6/2003 | Schulze et al. |
| 6,579,289 B2 | 6/2003 | Schnitzler |
| 6,582,424 B2 | 6/2003 | Fleenor et al. |
| 6,582,427 B1 | 6/2003 | Goble et al. |
| 6,584,360 B2 | 6/2003 | Francischelli et al. |
| D477,408 S | 7/2003 | Bromley |
| 6,585,732 B2 | 7/2003 | Mulier et al. |
| 6,585,733 B2 | 7/2003 | Wellman |
| 6,585,735 B1 | 7/2003 | Frazier et al. |
| 6,589,200 B1 | 7/2003 | Schwemberger et al. |
| 6,591,719 B1 | 7/2003 | Poole et al. |
| 6,592,582 B2 | 7/2003 | Hess et al. |
| 6,594,518 B1 | 7/2003 | Benaron et al. |
| 6,602,227 B1 | 8/2003 | Cimino et al. |
| 6,602,249 B1 | 8/2003 | Stoddard et al. |
| 6,602,252 B2 | 8/2003 | Mollenauer |
| 6,605,036 B1 | 8/2003 | Wild |
| 6,607,529 B1 | 8/2003 | Jones et al. |
| 6,610,060 B2 | 8/2003 | Mulier et al. |
| 6,611,793 B1 | 8/2003 | Burnside et al. |
| 6,613,048 B2 | 9/2003 | Mulier et al. |
| 6,616,656 B2 | 9/2003 | Brommersma |
| 6,616,660 B1 | 9/2003 | Platt |
| 6,616,661 B2 | 9/2003 | Wellman et al. |
| 6,620,157 B1 | 9/2003 | Dabney et al. |
| 6,620,161 B2 | 9/2003 | Schulze et al. |
| 6,623,482 B2 | 9/2003 | Pendekanti et al. |
| 6,623,515 B2 | 9/2003 | Mulier et al. |
| 6,626,901 B1 | 9/2003 | Treat et al. |
| 6,629,974 B2 | 10/2003 | Penny et al. |
| 6,638,274 B2 | 10/2003 | Yamamoto |
| 6,648,883 B2 | 11/2003 | Francischelli et al. |
| 6,652,514 B2 | 11/2003 | Ellman et al. |
| 6,652,521 B2 | 11/2003 | Schulze |
| 6,656,110 B1 | 12/2003 | Irion et al. |
| 6,656,175 B2 | 12/2003 | Francischelli et al. |
| 6,656,176 B2 | 12/2003 | Hess et al. |
| 6,656,177 B2 | 12/2003 | Truckai et al. |
| 6,660,017 B2 | 12/2003 | Beaupre |
| 6,662,050 B2 | 12/2003 | Olson |
| 6,662,127 B2 | 12/2003 | Wiener et al. |
| 6,663,622 B1 | 12/2003 | Foley et al. |
| 6,663,627 B2 | 12/2003 | Francischelli et al. |
| 6,663,628 B2 | 12/2003 | Peters |
| 6,666,865 B2 | 12/2003 | Platt |
| 6,676,660 B2 | 1/2004 | Wampler et al. |
| 6,678,621 B2 | 1/2004 | Wiener et al. |
| 6,679,882 B1 | 1/2004 | Kornerup |
| 6,682,527 B2 | 1/2004 | Strul |
| 6,682,528 B2 | 1/2004 | Frazier et al. |
| 6,682,544 B2 | 1/2004 | Mastri et al. |
| 6,685,701 B2 | 2/2004 | Orszulak et al. |
| 6,685,703 B2 | 2/2004 | Pearson et al. |
| 6,692,450 B1 | 2/2004 | Coleman |
| 6,692,489 B1 | 2/2004 | Heim et al. |
| 6,695,837 B2 | 2/2004 | Howell |
| 6,695,838 B2 | 2/2004 | Wellman et al. |
| 6,695,840 B2 | 2/2004 | Schulze |
| 6,699,240 B2 | 3/2004 | Francischelli |
| 6,706,038 B2 | 3/2004 | Francischelli et al. |
| 6,706,039 B2 | 3/2004 | Mulier et al. |
| 6,709,432 B2 | 3/2004 | Ferek-Petric |
| 6,723,091 B2 | 4/2004 | Goble et al. |
| 6,726,683 B1 | 4/2004 | Shaw |
| 6,726,686 B2 | 4/2004 | Buysse et al. |
| 6,733,498 B2 | 5/2004 | Paton et al. |
| 6,736,810 B2 | 5/2004 | Hoey et al. |
| 6,740,084 B2 | 5/2004 | Ryan |
| 6,740,085 B2 | 5/2004 | Hareyama et al. |
| 6,740,102 B2 | 5/2004 | Hess et al. |
| 6,743,229 B2 | 6/2004 | Buysse et al. |
| 6,752,804 B2 | 6/2004 | Simpson et al. |
| 6,755,825 B2 | 6/2004 | Schoenman et al. |
| 6,755,827 B2 | 6/2004 | Mulier et al. |
| 6,755,841 B2 | 6/2004 | Fraser et al. |
| 6,758,846 B2 | 7/2004 | Goble et al. |
| 6,764,487 B2 | 7/2004 | Mulier et al. |
| 6,770,071 B2 | 8/2004 | Woloszko et al. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,773,435 B2 | 8/2004 | Schulze et al. |
| 6,773,444 B2 | 8/2004 | Messerly |
| 6,775,575 B2 | 8/2004 | Bommannan et al. |
| 6,776,780 B2 | 8/2004 | Mulier et al. |
| 6,780,180 B1 | 8/2004 | Goble et al. |
| 6,786,906 B1 | 9/2004 | Cobb |
| 6,790,217 B2 | 9/2004 | Schulze et al. |
| 6,796,828 B2 | 9/2004 | Ehr et al. |
| 6,796,981 B2 | 9/2004 | Wham et al. |
| 6,807,444 B2 | 10/2004 | Tu et al. |
| 6,807,968 B2 | 10/2004 | Francischelli et al. |
| 6,808,518 B2 | 10/2004 | Wellman et al. |
| 6,808,525 B2 | 10/2004 | Latterell et al. |
| 6,814,745 B2 | 11/2004 | Prestel |
| 6,821,273 B2 | 11/2004 | Mollenauer |
| 6,827,715 B2 | 12/2004 | Francischelli et al. |
| 6,827,717 B2 | 12/2004 | Brommersma et al. |
| 6,827,725 B2 | 12/2004 | Batchelor et al. |
| 6,830,569 B2 | 12/2004 | Thompson et al. |
| 6,832,111 B2 | 12/2004 | Tu et al. |
| 6,832,985 B2 | 12/2004 | Irion et al. |
| 6,832,998 B2 | 12/2004 | Goble |
| 6,835,082 B2 | 12/2004 | Gonnering |

(56) References Cited

U.S. PATENT DOCUMENTS

| | | |
|---|---|---|
| 6,835,195 B2 | 12/2004 | Schulze et al. |
| 6,837,887 B2 | 1/2005 | Woloszko et al. |
| 6,843,789 B2 | 1/2005 | Goble |
| 6,849,073 B2 | 2/2005 | Hoey et al. |
| 6,852,112 B2 | 2/2005 | Platt |
| 6,855,142 B2 | 2/2005 | Harano et al. |
| 6,855,145 B2 | 2/2005 | Ciarrocca |
| 6,858,028 B2 | 2/2005 | Mulier et al. |
| 6,860,881 B2 | 3/2005 | Sturm et al. |
| 6,860,894 B1 | 3/2005 | Pittman |
| 6,887,240 B1 | 5/2005 | Lands et al. |
| 6,889,694 B2 | 5/2005 | Hooven |
| 6,893,435 B2 | 5/2005 | Goble |
| 6,893,441 B2 | 5/2005 | Brommersma et al. |
| 6,899,710 B2 | 5/2005 | Hooven |
| 6,905,497 B2 | 6/2005 | Truckai et al. |
| 6,905,498 B2 | 6/2005 | Hooven |
| 6,908,472 B2 | 6/2005 | Wiener et al. |
| 6,911,019 B2 | 6/2005 | Mulier et al. |
| 6,913,579 B2 | 7/2005 | Truckai et al. |
| 6,916,318 B2 | 7/2005 | Francischelli et al. |
| 6,918,880 B2 | 7/2005 | Brookner et al. |
| 6,923,803 B2 | 8/2005 | Goble |
| 6,923,804 B2 | 8/2005 | Eggers et al. |
| 6,923,806 B2 | 8/2005 | Hooven et al. |
| 6,926,716 B2 | 8/2005 | Baker et al. |
| 6,929,641 B2 | 8/2005 | Goble et al. |
| 6,929,644 B2 | 8/2005 | Truckai et al. |
| 6,932,810 B2 | 8/2005 | Ryan |
| 6,932,811 B2 | 8/2005 | Hooven et al. |
| 6,937,033 B2 | 8/2005 | Boronkay et al. |
| 6,939,347 B2 | 9/2005 | Thompson |
| 6,942,660 B2 | 9/2005 | Pantera et al. |
| 6,942,662 B2 | 9/2005 | Goble et al. |
| 6,945,972 B2 | 9/2005 | Frigg et al. |
| 6,945,981 B2 | 9/2005 | Donofrio et al. |
| 6,948,503 B2 | 9/2005 | Refior et al. |
| 6,949,098 B2 | 9/2005 | Mulier et al. |
| 6,958,063 B1 | 10/2005 | Soil et al. |
| 6,960,209 B2 | 11/2005 | Clague et al. |
| 6,960,210 B2 | 11/2005 | Lands et al. |
| 6,962,587 B2 | 11/2005 | Johnson et al. |
| 6,962,589 B2 | 11/2005 | Mulier et al. |
| 6,966,907 B2 | 11/2005 | Goble |
| 6,966,909 B2 | 11/2005 | Marshall et al. |
| 6,971,988 B2 | 12/2005 | Orban, III |
| 6,974,453 B2 | 12/2005 | Woloszko et al. |
| 6,974,454 B2 | 12/2005 | Hooven |
| 6,976,969 B2 | 12/2005 | Messerly |
| 6,979,332 B2 | 12/2005 | Adams |
| 6,984,231 B2 | 1/2006 | Goble et al. |
| 6,984,233 B2 | 1/2006 | Hooven |
| 6,984,826 B2 | 1/2006 | Miller et al. |
| 6,989,010 B2 | 1/2006 | Francischelli et al. |
| 6,994,705 B2 | 2/2006 | Nobis et al. |
| 6,997,735 B2 | 2/2006 | Ehr et al. |
| 6,997,935 B2 | 2/2006 | Anderson et al. |
| 7,001,380 B2 | 2/2006 | Goble |
| 7,001,415 B2 | 2/2006 | Hooven |
| 7,011,657 B2 | 3/2006 | Truckai et al. |
| 7,025,764 B2 | 4/2006 | Paton et al. |
| 7,029,470 B2 | 4/2006 | Francischelli et al. |
| 7,033,351 B2 | 4/2006 | Howell |
| 7,033,354 B2 | 4/2006 | Keppel |
| 7,033,356 B2 | 4/2006 | Latterell et al. |
| 7,041,096 B2 | 5/2006 | Malis et al. |
| 7,041,102 B2 | 5/2006 | Truckai et al. |
| 7,044,948 B2 | 5/2006 | Keppel |
| 7,044,949 B2 | 5/2006 | Orszulak et al. |
| 7,044,950 B2 | 5/2006 | Yamamoto |
| 7,048,687 B1 | 5/2006 | Reuss et al. |
| 7,049,599 B2 | 5/2006 | Miller et al. |
| 7,052,494 B2 | 5/2006 | Goble et al. |
| 7,060,063 B2 | 6/2006 | Marion et al. |
| 7,063,699 B2 | 6/2006 | Hess et al. |
| 7,066,933 B2 | 6/2006 | Hagg |
| 7,066,936 B2 | 6/2006 | Ryan |
| 7,070,597 B2 | 7/2006 | Truckai et al. |
| 7,074,218 B2 | 7/2006 | Washington et al. |
| 7,074,219 B2 | 7/2006 | Levine et al. |
| 7,083,618 B2 | 8/2006 | Couture et al. |
| 7,083,619 B2 | 8/2006 | Truckai et al. |
| 7,083,620 B2 | 8/2006 | Jahns et al. |
| 7,087,054 B2 | 8/2006 | Truckai et al. |
| 7,090,673 B2 | 8/2006 | Dycus et al. |
| 7,094,202 B2 | 8/2006 | Nobis et al. |
| 7,094,235 B2 | 8/2006 | Francischelli |
| 7,097,644 B2 | 8/2006 | Long |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,104,834 B2 | 9/2006 | Robinson et al. |
| 7,104,989 B2 | 9/2006 | Skarda |
| 7,108,695 B2 | 9/2006 | Witt et al. |
| 7,111,769 B2 | 9/2006 | Wales et al. |
| 7,112,201 B2 | 9/2006 | Truckai et al. |
| RE39,358 E | 10/2006 | Goble |
| 7,116,157 B2 | 10/2006 | Ross et al. |
| 7,118,564 B2 | 10/2006 | Ritchie et al. |
| 7,118,570 B2 | 10/2006 | Tetzlaff et al. |
| 7,118,587 B2 | 10/2006 | Dycus et al. |
| 7,119,516 B2 | 10/2006 | Denning |
| 7,124,932 B2 | 10/2006 | Isaacson |
| 7,125,409 B2 | 10/2006 | Truckai et al. |
| 7,126,125 B2 | 10/2006 | Miller et al. |
| 7,131,445 B2 | 11/2006 | Amoah |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,018 B2 | 11/2006 | Ryan et al. |
| 7,135,020 B2 | 11/2006 | Lawes et al. |
| 7,137,980 B2 | 11/2006 | Buysse et al. |
| D533,942 S | 12/2006 | Kerr et al. |
| 7,147,635 B2 | 12/2006 | Ciarrocca |
| 7,147,637 B2 | 12/2006 | Goble |
| 7,147,638 B2 | 12/2006 | Chapman et al. |
| 7,150,097 B2 | 12/2006 | Sremcich et al. |
| 7,150,748 B2 | 12/2006 | Ebbutt et al. |
| 7,150,749 B2 | 12/2006 | Dycus et al. |
| 7,153,300 B2 | 12/2006 | Goble |
| 7,156,843 B2 | 1/2007 | Skarda |
| 7,156,845 B2 | 1/2007 | Mulier et al. |
| 7,156,846 B2 | 1/2007 | Dycus et al. |
| 7,159,750 B2 | 1/2007 | Racenet et al. |
| 7,160,293 B2 | 1/2007 | Sturm et al. |
| 7,160,298 B2 | 1/2007 | Lawes et al. |
| 7,160,299 B2 | 1/2007 | Baily |
| 7,163,548 B2 | 1/2007 | Stulen et al. |
| 7,166,105 B2 | 1/2007 | Mulier et al. |
| 7,169,115 B2 | 1/2007 | Nobis et al. |
| 7,169,144 B2 | 1/2007 | Hoey et al. |
| 7,169,145 B2 | 1/2007 | Isaacson et al. |
| 7,169,146 B2 | 1/2007 | Truckai et al. |
| 7,172,591 B2 | 2/2007 | Harano et al. |
| 7,179,254 B2 | 2/2007 | Pendkanti et al. |
| 7,179,258 B2 | 2/2007 | Buysse et al. |
| 7,182,604 B2 | 2/2007 | Ehr et al. |
| 7,186,252 B2 | 3/2007 | Nobis et al. |
| 7,186,253 B2 | 3/2007 | Truckai et al. |
| 7,187,790 B2 | 3/2007 | Sabol et al. |
| 7,189,231 B2 | 3/2007 | Clague et al. |
| 7,189,232 B2 | 3/2007 | Scholl et al. |
| 7,189,233 B2 | 3/2007 | Truckai et al. |
| 7,191,015 B2 | 3/2007 | Lamson et al. |
| 7,195,627 B2 | 3/2007 | Amoah et al. |
| 7,195,630 B2 | 3/2007 | Ciarrocca |
| 7,195,631 B2 | 3/2007 | Dumbauld |
| 7,204,835 B2 | 4/2007 | Latterell et al. |
| 7,207,471 B2 | 4/2007 | Heinrich et al. |
| 7,207,990 B2 | 4/2007 | Lands et al. |
| D541,938 S | 5/2007 | Kerr et al. |
| 7,211,081 B2 | 5/2007 | Goble |
| 7,211,084 B2 | 5/2007 | Goble et al. |

(56) References Cited

U.S. PATENT DOCUMENTS

| | | |
|---|---|---|
| 7,214,224 B2 | 5/2007 | Goble |
| 7,216,001 B2 | 5/2007 | Hacker et al. |
| 7,220,260 B2 | 5/2007 | Fleming et al. |
| 7,220,951 B2 | 5/2007 | Truckai et al. |
| 7,223,239 B2 | 5/2007 | Schulze et al. |
| 7,223,265 B2 | 5/2007 | Keppel |
| 7,226,447 B2 | 6/2007 | Uchida et al. |
| 7,229,307 B2 | 6/2007 | Ehr et al. |
| 7,232,439 B2 | 6/2007 | Ciarrocca |
| 7,232,440 B2 | 6/2007 | Aid et al. |
| 7,235,048 B2 | 6/2007 | Rein et al. |
| 7,235,072 B2 | 6/2007 | Sartor et al. |
| 7,235,073 B2 | 6/2007 | Levine et al. |
| 7,237,708 B1 | 7/2007 | Guy et al. |
| 7,241,296 B2 | 7/2007 | Buysse et al. |
| 7,247,141 B2 | 7/2007 | Makin et al. |
| 7,247,155 B2 | 7/2007 | Hoey et al. |
| 7,250,048 B2 | 7/2007 | Francischelli et al. |
| 7,250,051 B2 | 7/2007 | Francischelli |
| 7,252,667 B2 | 8/2007 | Moses et al. |
| 7,255,694 B2 | 8/2007 | Keppel |
| 7,255,696 B2 | 8/2007 | Goble et al. |
| 7,255,697 B2 | 8/2007 | Dycus et al. |
| 7,259,340 B2 | 8/2007 | Blaha et al. |
| 7,261,711 B2 | 8/2007 | Mulier et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,273,483 B2 | 9/2007 | Weiner et al. |
| 7,276,068 B2 | 10/2007 | Johnson et al. |
| 7,278,994 B2 | 10/2007 | Goble |
| 7,282,048 B2 | 10/2007 | Goble et al. |
| 7,282,049 B2 | 10/2007 | Oraszulak et al. |
| 7,291,161 B2 | 11/2007 | Hooven |
| 7,297,145 B2 | 11/2007 | Woloszko et al. |
| 7,300,435 B2 | 11/2007 | Wham et al. |
| 7,300,446 B2 | 11/2007 | Beaupre |
| 7,300,450 B2 | 11/2007 | Vleugels et al. |
| 7,303,557 B2 | 12/2007 | Wham et al. |
| 7,309,325 B2 | 12/2007 | Mulier et al. |
| 7,309,849 B2 | 12/2007 | Truckai et al. |
| 7,311,560 B2 | 12/2007 | Ehr et al. |
| 7,311,706 B2 | 12/2007 | Schoenman et al. |
| 7,311,707 B2 | 12/2007 | Hagg et al. |
| 7,311,709 B2 | 12/2007 | Truckai et al. |
| 7,322,975 B2 | 1/2008 | Goble et al. |
| 7,329,256 B2 | 2/2008 | Johnson et al. |
| 7,335,997 B2 | 2/2008 | Weiner |
| 7,344,532 B2 | 3/2008 | Goble et al. |
| 7,347,858 B2 | 3/2008 | Francischelli et al. |
| RE40,279 E | 4/2008 | Sluijter et al. |
| D567,943 S | 4/2008 | Moses et al. |
| 7,353,068 B2 | 4/2008 | Tanaka et al. |
| 7,354,435 B2 | 4/2008 | Farin et al. |
| 7,354,440 B2 | 4/2008 | Truckal et al. |
| 7,354,443 B2 | 4/2008 | Moll et al. |
| 7,364,577 B2 | 4/2008 | Wham et al. |
| 7,364,578 B2 | 4/2008 | Francischelli et al. |
| 7,364,579 B2 | 4/2008 | Mulier et al. |
| 7,367,972 B2 | 5/2008 | Francischelli et al. |
| 7,367,976 B2 | 5/2008 | Lawes et al. |
| 7,371,246 B2 | 5/2008 | Viola |
| 7,377,902 B2 | 5/2008 | Burbank et al. |
| 7,377,918 B2 | 5/2008 | Amoah |
| 7,377,920 B2 | 5/2008 | Buysse et al. |
| RE40,388 E | 6/2008 | Gines |
| 7,381,209 B2 | 6/2008 | Truckai et al. |
| 7,384,420 B2 | 6/2008 | Dycus et al. |
| 7,384,421 B2 | 6/2008 | Hushka |
| 7,396,336 B2 | 7/2008 | Orszulak et al. |
| D575,395 S | 8/2008 | Hushka |
| D575,401 S | 8/2008 | Hixson et al. |
| 7,416,101 B2 | 8/2008 | Shelton, IV et al. |
| 7,416,437 B2 | 8/2008 | Sartor et al. |
| 7,419,487 B2 | 9/2008 | Johnson et al. |
| 7,422,139 B2 | 9/2008 | Shelton, IV et al. |
| 7,422,588 B2 | 9/2008 | Mulier et al. |
| 7,424,965 B2 | 9/2008 | Racenet et al. |
| 7,425,835 B2 | 9/2008 | Eisele |
| 7,426,415 B2 | 9/2008 | Kühner |
| 7,431,720 B2 | 10/2008 | Pendekanti et al. |
| 7,431,721 B2 | 10/2008 | Paton et al. |
| 7,435,249 B2 | 10/2008 | Buysse et al. |
| 7,435,250 B2 | 10/2008 | Francischelli et al. |
| 7,442,167 B2 | 10/2008 | Dunki-Jacobs et al. |
| 7,442,193 B2 | 10/2008 | Shields et al. |
| 7,442,194 B2 | 10/2008 | Dumbauld et al. |
| 7,445,621 B2 | 11/2008 | Dumbauld et al. |
| 7,458,972 B2 | 12/2008 | Keppel |
| 7,464,846 B2 | 12/2008 | Shelton, IV et al. |
| 7,470,272 B2 | 12/2008 | Mulier et al. |
| 7,473,250 B2 | 1/2009 | Makin et al. |
| 7,473,253 B2 | 1/2009 | Dycus et al. |
| 7,476,233 B1 | 1/2009 | Wiener et al. |
| 7,481,808 B2 | 1/2009 | Koyfman et al. |
| 7,491,199 B2 | 2/2009 | Goble |
| 7,497,858 B2 | 3/2009 | Chapelon et al. |
| 7,811,283 B2 | 10/2010 | Moses et al. |
| 7,841,765 B2 | 11/2010 | Keller |
| 8,561,615 B2 | 10/2013 | Pannell et al. |
| 8,784,417 B2 | 7/2014 | Hanna |
| 8,808,288 B2 | 8/2014 | Rescheke |
| 9,161,813 B2 | 10/2015 | Benamou |
| 2001/0037110 A1 | 11/2001 | Schmaltz et al. |
| 2001/0039417 A1 | 11/2001 | Harano et al. |
| 2002/0052599 A1 | 5/2002 | Goble |
| 2002/0115997 A1 | 8/2002 | Truckai et al. |
| 2002/0120262 A1 | 8/2002 | Bek et al. |
| 2002/0120266 A1 | 8/2002 | Truckai et al. |
| 2002/0128650 A1 | 9/2002 | McClurken |
| 2002/0151884 A1 | 10/2002 | Hoey et al. |
| 2002/0161363 A1 | 10/2002 | Fodor et al. |
| 2002/0165541 A1 | 11/2002 | Whitman |
| 2002/0188294 A1 | 12/2002 | Couture et al. |
| 2003/0004510 A1 | 1/2003 | Wham et al. |
| 2003/0014052 A1 | 1/2003 | Buysse et al. |
| 2003/0060818 A1 | 3/2003 | Kannenberg et al. |
| 2003/0065327 A1 | 4/2003 | Wellman et al. |
| 2003/0065358 A1 | 4/2003 | Frecker et al. |
| 2003/0069571 A1 | 4/2003 | Treat et al. |
| 2003/0109871 A1 | 6/2003 | Johnson et al. |
| 2003/0114845 A1 | 6/2003 | Paton et al. |
| 2003/0114848 A1 | 6/2003 | Cobb |
| 2003/0114851 A1 | 6/2003 | Truckai et al. |
| 2003/0125728 A1 | 7/2003 | Nezhat et al. |
| 2003/0125731 A1 | 7/2003 | Smith et al. |
| 2003/0125734 A1 | 7/2003 | Mollenauer |
| 2003/0139741 A1 | 7/2003 | Goble et al. |
| 2003/0181910 A1 | 9/2003 | Dycus et al. |
| 2003/0199863 A1 | 10/2003 | Swanson et al. |
| 2003/0199870 A1 | 10/2003 | Truckai et al. |
| 2003/0229344 A1 | 12/2003 | Dycus et al. |
| 2003/0236549 A1 | 12/2003 | Bonadio et al. |
| 2004/0006340 A1 | 1/2004 | Latterell et al. |
| 2004/0010289 A1 | 1/2004 | Biggs et al. |
| 2004/0068274 A1 | 4/2004 | Hooven |
| 2004/0068304 A1 | 4/2004 | Paton et al. |
| 2004/0073247 A1 | 4/2004 | Loshakove et al. |
| 2004/0082946 A1 | 4/2004 | Malis et al. |
| 2004/0092922 A1 | 5/2004 | Kadziauskas et al. |
| 2004/0122423 A1 | 6/2004 | Dycus et al. |
| 2004/0162557 A1 | 8/2004 | Tetzlaff et al. |
| 2004/0193148 A1 | 9/2004 | Wham et al. |
| 2004/0215127 A1 | 10/2004 | Kadziauskas et al. |
| 2004/0225288 A1 | 11/2004 | Buysse et al. |
| 2004/0250419 A1 | 12/2004 | Sremich et al. |
| 2005/0004563 A1 | 1/2005 | Racz et al. |
| 2005/0004564 A1 | 1/2005 | Wham et al. |
| 2005/0015125 A1 | 1/2005 | Mioduski et al. |
| 2005/0021027 A1 | 1/2005 | Shields et al. |
| 2005/0033282 A1 | 2/2005 | Hooven |
| 2005/0033352 A1 | 2/2005 | Zepf et al. |
| 2005/0080319 A1 | 4/2005 | Dinkler, II et al. |
| 2005/0090815 A1 | 4/2005 | Francischelli et al. |

(56) References Cited

U.S. PATENT DOCUMENTS

| | | |
|---|---|---|
| 2005/0096681 A1 | 5/2005 | Desinger et al. |
| 2005/0101951 A1 | 5/2005 | Wham et al. |
| 2005/0107785 A1 | 5/2005 | Dycus et al. |
| 2005/0113817 A1 | 5/2005 | Isaacson et al. |
| 2005/0113819 A1 | 5/2005 | Wham et al. |
| 2005/0124915 A1 | 6/2005 | Eggers et al. |
| 2005/0124987 A1 | 6/2005 | Goble |
| 2005/0137592 A1 | 6/2005 | Nguyen et al. |
| 2005/0149017 A1 | 7/2005 | Dycus |
| 2005/0159745 A1 | 7/2005 | Truckai et al. |
| 2005/0165444 A1 | 7/2005 | Hart et al. |
| 2005/0192568 A1 | 9/2005 | Truckai et al. |
| 2005/0203504 A1 | 9/2005 | Wham et al. |
| 2005/0234447 A1 | 10/2005 | Paton et al. |
| 2005/0245918 A1 | 11/2005 | Sliwa, Jr. et al. |
| 2005/0245922 A1 | 11/2005 | Goble |
| 2006/0020265 A1 | 1/2006 | Ryan |
| 2006/0041254 A1 | 2/2006 | Francischelli et al. |
| 2006/0052777 A1 | 3/2006 | Dumbauld |
| 2006/0079788 A1 | 4/2006 | Anderson et al. |
| 2006/0079878 A1 | 4/2006 | Houser |
| 2006/0129146 A1 | 6/2006 | Dycus et al. |
| 2006/0161190 A1 | 7/2006 | Gadberry et al. |
| 2006/0167450 A1 | 7/2006 | Johnson et al. |
| 2006/0173453 A1 | 8/2006 | Gruhl et al. |
| 2006/0217697 A1 | 9/2006 | Lau et al. |
| 2006/0217706 A1 | 9/2006 | Lau et al. |
| 2006/0217707 A1 | 9/2006 | Daniel et al. |
| 2006/0224152 A1 | 10/2006 | Behnke et al. |
| 2006/0224158 A1 | 10/2006 | Odom et al. |
| 2006/0247498 A1 | 11/2006 | Bonadio et al. |
| 2006/0271042 A1 | 11/2006 | Latterell et al. |
| 2007/0016185 A1 | 1/2007 | Tullis et al. |
| 2007/0043352 A1 | 2/2007 | Garrison et al. |
| 2007/0043353 A1 | 2/2007 | Dycus et al. |
| 2007/0062017 A1 | 3/2007 | Dycus et al. |
| 2007/0088202 A1 | 4/2007 | Albrecht et al. |
| 2007/0090788 A1 | 4/2007 | Hansford et al. |
| 2007/0093800 A1 | 4/2007 | Wham et al. |
| 2007/0123847 A1 | 5/2007 | Mihori |
| 2007/0135811 A1 | 6/2007 | Hooven |
| 2007/0142833 A1 | 6/2007 | Dycus et al. |
| 2007/0142834 A1 | 6/2007 | Dumbauld |
| 2007/0156139 A1 | 7/2007 | Schecter et al. |
| 2007/0156140 A1 | 7/2007 | Baily |
| 2007/0167941 A1 | 7/2007 | Hamel et al. |
| 2007/0173811 A1 | 7/2007 | Couture et al. |
| 2007/0173813 A1 | 7/2007 | Odom |
| 2007/0173814 A1 | 7/2007 | Hixson et al. |
| 2007/0179499 A1 | 8/2007 | Garrison |
| 2007/0191827 A1 | 8/2007 | Lischinsky et al. |
| 2007/0191828 A1 | 8/2007 | Houser et al. |
| 2007/0203481 A1 | 8/2007 | Gregg et al. |
| 2007/0213712 A1 | 9/2007 | Buysse et al. |
| 2007/0260242 A1 | 11/2007 | Dycus et al. |
| 2007/0276363 A1 | 11/2007 | Patton et al. |
| 2007/0282195 A1 | 12/2007 | Masini et al. |
| 2007/0282320 A1 | 12/2007 | Buysse et al. |
| 2007/0282332 A1 | 12/2007 | Witt et al. |
| 2007/0287997 A1 | 12/2007 | Tolmei |
| 2008/0009860 A1 | 1/2008 | Odom |
| 2008/0015563 A1 | 1/2008 | Hoey et al. |
| 2008/0015564 A1 | 1/2008 | Wham et al. |
| 2008/0015567 A1 | 1/2008 | Kimura |
| 2008/0030206 A1 | 2/2008 | Podhajsky et al. |
| 2008/0039831 A1 | 2/2008 | Odom et al. |
| 2008/0045947 A1 | 2/2008 | Johnson et al. |
| 2008/0058802 A1 | 3/2008 | Couture et al. |
| 2008/0082095 A1* | 4/2008 | Shores ............ A61B 18/1206 606/34 |
| 2008/0082098 A1 | 4/2008 | Tanaka et al. |
| 2008/0091189 A1 | 4/2008 | Carlton |
| 2008/0114356 A1 | 5/2008 | Johnson et al. |
| 2008/0125772 A1 | 5/2008 | Stone et al. |
| 2008/0132893 A1 | 6/2008 | D'Amelio et al. |
| 2008/0167651 A1 | 7/2008 | Tetzlaff et al. |
| 2008/0172048 A1 | 7/2008 | Martin et al. |
| 2008/0188848 A1 | 8/2008 | Deutmeyer et al. |
| 2008/0208246 A1 | 8/2008 | Livneh |
| 2008/0215050 A1 | 9/2008 | Bakos |
| 2008/0215051 A1 | 9/2008 | Buysse et al. |
| 2008/0221565 A1 | 9/2008 | Eder et al. |
| 2008/0228179 A1 | 9/2008 | Eder et al. |
| 2008/0294222 A1 | 11/2008 | Schecter |
| 2008/0300589 A1 | 12/2008 | Paul et al. |
| 2008/0300590 A1 | 12/2008 | Horne et al. |
| 2008/0300591 A1 | 12/2008 | Darian et al. |
| 2009/0012520 A1 | 1/2009 | Hixson et al. |
| 2009/0024126 A1 | 1/2009 | Artale et al. |
| 2009/0030477 A1* | 1/2009 | Jarrard ............... A61B 18/14 607/42 |
| 2009/0171352 A1 | 7/2009 | Sutter |
| 2009/0248007 A1 | 10/2009 | Falkenstein et al. |
| 2009/0275490 A1 | 11/2009 | Milne et al. |
| 2009/0275940 A1 | 11/2009 | Malackowski et al. |
| 2012/0010614 A1 | 1/2012 | Couture |
| 2012/0059371 A1 | 3/2012 | Anderson et al. |
| 2012/0083785 A1 | 4/2012 | Roy et al. |
| 2012/0136347 A1 | 5/2012 | Brustad et al. |
| 2012/0197243 A1 | 8/2012 | Sherman et al. |
| 2012/0215220 A1 | 8/2012 | Manzo et al. |
| 2013/0018411 A1 | 1/2013 | Collings et al. |
| 2013/0138101 A1 | 5/2013 | Kerr |
| 2013/0138102 A1 | 5/2013 | Twomey et al. |
| 2013/0197874 A1 | 8/2013 | Heckel |
| 2013/0267951 A1 | 10/2013 | Twomey |
| 2013/0274743 A1 | 10/2013 | Banfalvi |
| 2013/0296843 A1 | 11/2013 | Boudreaux et al. |
| 2013/0345696 A1 | 12/2013 | Behnke, II et al. |
| 2014/0005658 A1 | 1/2014 | Rosenbegr |
| 2014/0088575 A1 | 3/2014 | Singh |
| 2014/0214019 A1 | 7/2014 | Baxter, III et al. |
| 2014/0254221 A1* | 9/2014 | Johnson ........... A61B 18/1206 363/98 |
| 2016/0000495 A1* | 1/2016 | Elliott ............... A61B 18/1445 606/34 |
| 2016/0058492 A1 | 3/2016 | Yates et al. |
| 2016/0151107 A1* | 6/2016 | Wham ............ A61B 18/1206 700/287 |
| 2016/0310203 A1 | 10/2016 | Gaspredes et al. |
| 2016/0310204 A1 | 10/2016 | McHenry et al. |
| 2018/0256242 A1* | 9/2018 | Bluvshtein ........ H02M 7/53873 |

FOREIGN PATENT DOCUMENTS

| | | |
|---|---|---|
| DE | 10 2005 044 918 A1 | 2/2007 |
| EP | 0 315 338 A1 | 5/1989 |
| EP | 0 538 984 A2 | 4/1993 |
| EP | 0 570 675 B1 | 11/1993 |
| EP | 0 598 202 B1 | 5/1994 |
| EP | 0 717 967 A2 | 6/1996 |
| EP | 0 737 447 A1 | 10/1996 |
| EP | 0 878 168 A1 | 11/1998 |
| EP | 1 054 637 B1 | 11/2000 |
| EP | 1 157 666 A1 | 11/2001 |
| EP | 1 500 378 A1 | 1/2005 |
| EP | 1 535 581 A2 | 6/2005 |
| EP | 1 545 361 B1 | 6/2005 |
| EP | 1 557 129 A1 | 7/2005 |
| EP | 1 634 539 A1 | 3/2006 |
| EP | 1 634 539 B1 | 3/2006 |
| EP | 1 665 995 A1 | 6/2006 |
| EP | 1 728 475 A2 | 12/2006 |
| EP | 1 810 628 A1 | 7/2007 |
| EP | 1 946 715 A1 | 7/2008 |
| EP | 2 106 762 A1 | 10/2009 |
| EP | 2 111 812 A2 | 10/2009 |
| EP | 2 156 802 A2 | 2/2010 |
| EP | 2 301 462 A1 | 3/2011 |
| EP | 2 340 792 A1 | 7/2011 |
| EP | 2 436 327 A1 | 4/2012 |
| EP | 2 436 330 A1 | 4/2012 |
| EP | 2 574 300 A1 | 4/2013 |

(56) References Cited

FOREIGN PATENT DOCUMENTS

| | | |
|---|---|---|
| EP | 2 712 568 A2 | 4/2014 |
| EP | 2 777 578 A1 | 9/2014 |
| EP | 3 369 392 A2 | 9/2018 |
| GB | 2 157 175 A | 10/1985 |
| GB | 2 462 453 A | 8/2008 |
| JP | 60-30946 A | 2/1994 |
| JP | 83-17935 A | 12/1996 |
| JP | 11-070123 A | 3/1999 |
| JP | 11-070124 A | 3/1999 |
| JP | 11-178833 A | 7/1999 |
| JP | 2000-254135 A | 9/2000 |
| JP | 2003-135481 A | 5/2003 |
| JP | 2003-164463 A | 6/2003 |
| JP | 2006-109945 A | 4/2006 |
| JP | 2006-167403 A | 6/2006 |
| JP | 2007-144201 A | 6/2007 |
| JP | 2007-195980 A | 8/2007 |
| JP | 2007-195985 A | 8/2007 |
| JP | 2008-043789 A | 2/2008 |
| JP | 2008-259864 A | 10/2008 |
| WO | WO 93/015662 A1 | 8/1993 |
| WO | WO 97/010764 A1 | 3/1997 |
| WO | WO 99/040857 A1 | 8/1999 |
| WO | WO 01/012090 A1 | 2/2001 |
| WO | WO 2004/030553 A1 | 4/2004 |
| WO | WO 2004/032776 A1 | 4/2004 |
| WO | WO 2004/032777 A1 | 4/2004 |
| WO | WO 2004/082495 A1 | 9/2004 |
| WO | WO 2005/004735 A1 | 1/2005 |
| WO | WO 05/053785 A2 | 6/2005 |
| WO | WO 2006/119245 A2 | 11/2006 |
| WO | WO 2006/125558 A1 | 11/2006 |
| WO | WO 2007/044849 A1 | 4/2007 |
| WO | WO 2007/142601 A1 | 12/2007 |
| WO | WO 2008/147773 A1 | 12/2008 |
| WO | WO 2009/065140 A1 | 5/2009 |
| WO | WO 2012/110996 A2 | 8/2012 |
| WO | WO 2013/030349 A1 | 3/2013 |

OTHER PUBLICATIONS

International Searching Authority/US, The International Search Report and the Written Opinion for International Application No. PCT/US2019/059909 titled "Electrosurgical System," dated Apr. 28, 2020, 23 pgs.
International Searching Authority/US, The International Search Report and the Written Opinion for International Application No. PCT/US2019/049768 titled "Electrosurgical Generator Verification System." dated Dec. 11, 2019, 19 pgs.
European Patent Office, Invitation to Pay Additional Fees for International Application No. PCT/US2019/049807, titled "Electrosurgical Generator Control System", dated Dec. 19, 2019, 16 pgs.
European Patent Office, Extended European Search Report for European Patent No. 19198318.8, entitled, "Bipolar Electrosurgical Sealer and Divider," dated Dec. 17, 2019, 10 pgs.
International Searching Authority/US, The International Search Report and the Written Opinion for International Application No. PCT/US2019/049807 titled "Electrosurgical Generator Control System." dated Feb. 12, 2020, 20 pgs.
International Preliminary Examining Authority/US, International Preliminary Report on Patentability for International Application No. PCT/US2019/049768, titled "Electrosurgical Generator Verification System," dated Mar. 18, 2021, 13 pgs.
International Preliminary Examining Authority/US, International Preliminary Report on Patentability for International Application No. PCT/US2019/049807, titled "Electrosurgical Generator Control System," dated Mar. 18, 2021, 13 pgs.
Bertil Vallfors and Bjorn Bergdahl, Automatically controlled bipolar electrocoagulation—"COA-COMP", Neurosug. Rev., 1984, pp. 187-190.

"New Products" Journal of Medical Engineering and Technology, vol. 19, No. 5 (Sep./Oct. 1995), pp. 189-190.
International Searching Authority/US, The International Search Report and the Written Opinion for International Application No. PCT/US09/39046 titled "Electrosurgical System," dated Jul. 27, 2009, 31 pgs.
International Preliminary Examining Authority/US, International Preliminary Report on Patentability for International Application No. PCT/US09/39046, titled "Electrosurgical System," dated Mar. 26, 2010, 18 pgs.
European Patent Office, European Search Report for European Application No. EP 10 19 2593, titled "Electrosurgical System," dated Mar. 21, 2011, 8 pgs.
European Patent Office, European Search Report for European Application No. EP 10 19 2614, titled "Electrosurgical System," dated Apr. 18, 2011, 7 pgs.
European Patent Office, Extended European Search Report for European Application No. EP 10 19 2580, dated Jul. 21, 2011, 6 pgs.
International Preliminary Examining Authority/US, International Preliminary Report on Patentability for International Application No. PCT/US09/39046, titled "Electrosurgical System," dated Jan. 17, 2012, 45 pgs.
European Patent Office, European Search Report for European Patenet Application No. 12151288, dated Feb. 10, 2012, 8 pgs.
European Patent Office, The International Search Report and Written Opinion of the International Searching Authority for International Application No. PCT/US2011/054661, dated Mar. 6, 2012, 23 pgs.
European Patent Office, Supplementary European Search Report for European Patent Application No. 08755322, dated Apr. 18, 2012, 3 pgs.
European Patent Office, Supplementary European Search Report for European Patent Application No. 08755322, dated Jun. 6, 2012, 2 pgs.
European Patent Office, Partial European Search Report for European Patent Application No. 15151398.3, dated Jun. 22, 2015, 9 pgs.
U.S. Appl. No. 12/611,352, filed Nov. 3, 2009, titled Tissue Fusion/Welder Apparatus and Method, now U.S. Pat. No. 8,551,089 issued Oct. 8, 2013.
U.S. Appl. No. 12/183,970, filed Jul. 31, 2008, entitled Bipolar Electrosurgical Scissors, now U.S. Pat. No. 8,226,649 issued Jul. 24, 2012.
U.S. Appl. No. 12/416,128, filed Mar. 31, 2009, entitled Electrosurgical System, now U.S. Pat. No. 8,568,411 issued Oct. 29, 2013.
US Patent Application No. PCT/US09/39046 filed Mar. 31, 2009, entitled Electrosurgical System.
U.S. Appl. No. 12/416,668, filed Apr. 1, 2009, entitled Electrosurgical System, now U.S. Pat. No. 8,562,598 issued Oct. 22, 2013.
U.S. Appl. No. 12/416,695, filed Apr. 1, 2009, entitled Electrosurgical System, now U.S. Pat. No. 8,551,088 issued Oct. 8, 2013.
U.S. Appl. No. 12/416,765, filed Apr. 1, 2009, entitled Electrosurgical System, now U.S. Pat. No. 8,915,910 issued Dec. 23, 2014.
U.S. Appl. No. 12/416,751, filed Apr. 1, 2009, entitled Electrosurgical System, now U.S. Pat. No. 8,579,894 issued Nov. 12, 2013.
The International Bureau of WIPO, The International Preliminary Report on Patentability for International Application No. PCT/US2011/054661, entitled "Electrosurgical Instruments and Connections Thereto," dated Apr. 2, 2013, 10 pgs.
European Patent Office, European Search Report for European Application No. EP 13 17 4814.7, titled "Electrosurgical System," dated Sep. 30, 2013, 4 pgs.
European Patent Office, European Search Report for European Patent Application No. EP 14199708.0, entitled "Electrosurgical System," dated Jul. 10, 2015, 14 pgs.
International Searching Authority/US, The International Search Report and the Written Opinion for International Application No. PCT/US2015/031452 ,titled "Electrosurgical Fusion Device," dated Dec. 3, 2015, 27 pgs.
International Searching Authority/US, The International Search Report and the Written Opinion for International Application No. PCT/US2015/066473 titled "Bipolar Electrosurgical Sealer and Divider." dated Mar. 31, 2016, 13 pgs.

(56) References Cited

OTHER PUBLICATIONS

International Searching Authority/US, The International Search Report and the Written Opinion for International Application No. PCT/US2015/033546 titled "Electrosurgical Seal and Dissection Systems." dated Apr. 22, 2016, 31 pgs.

International Preliminary Examining Authority/US, International Preliminary Report on Patentability for International Application No. PCT/US2015/031452, titled "Electrosurgical System," dated Dec. 1, 2016, 21 pgs.

International Preliminary Examining Authority/US, International Preliminary Report on Patentability for International Application No. PCT/US2015/033546, titled "Electrosurgical Laparoscopic Sealer and Dissector," dated Dec. 15, 2016, 22 pgs.

International Preliminary Examining Authority/US, International Preliminary Report on Patentability for International Application No. PCT/US2015/0066473, titled "Bipolar Electrosurgical Sealer and Divider," dated Jul. 6, 2017, 10 pgs.

European Patent Office, Extended European Search Report for European Application No. EP 17207793.5, dated May 16, 2018, 9 pgs.

European Patent Office, Extended European Search Report for European Application No. EP 18165110.0, dated Jun. 13, 2018, 6 pgs.

European Patent Office, Extended European Search Report for European Application No. EP 21215386.0, dated May 24, 2022, 6 pgs.

European Patent Office, The International Search Report and Written Opinion for International Application No. PCT/US2020/067540, dated May 3, 2021, entitled "Electrosurgical System with Tissue and Maximum Current Identification," 12 pages.

International Preliminary Examining Authority/US, International Preliminary Report on Patentability for International Application No. PCT/US2020/067540, titled "Electrosurgical System with Tissue and Maximum Current Identification," dated Jul. 14, 2022, 9 pgs.

* cited by examiner

ELECTROSURGICAL GENERATOR CONTROL SYSTEM

CROSS-REFERENCE TO RELATED APPLICATIONS

This application claims the benefit of and is a non-provisional of U.S. Provisional Application Ser. No. 62/727,195 filed on Sep. 5, 2018, which is hereby expressly incorporated by reference in its entirety for all purposes.

TECHNICAL FIELD

The present disclosure is generally directed to electrosurgical generator systems and methods and more particularly to electrosurgical control systems configured for regulating dynamically the generator's output to provide optimal radiofrequency (RF) energy for sealing, fusing and/or cutting tissues or vessels

BACKGROUND

Electrosurgical hand devices or instruments have become available that use radiofrequency (RF) energy to perform certain surgical tasks. Electrosurgical instruments may include one or more electrodes that are configured to be supplied with electrical energy from an electrosurgical generator. The electrical energy can be used to fuse, seal, or cut tissue to which it is applied. Examples of such electrosurgical or surgical instruments may include graspers, scissors, tweezers, blades or needles.

Electrosurgical instruments typically fall within two classifications: monopolar and bipolar. In monopolar instruments, electrical energy is supplied to one or more electrodes on the instrument with high current density while a separate return electrode is electrically coupled to a patient and is often designed to minimize current density. Monopolar electrosurgical instruments can be useful in certain procedures, but can include a risk of certain types of patient injuries such as electrical burns often at least partially attributable to functioning of the return electrode. In bipolar electrosurgical instruments, one or more electrodes is electrically coupled to a source of electrical energy of a first polarity and one or more other electrodes is electrically coupled to a source of electrical energy of a second polarity opposite the first polarity. Bipolar electrosurgical instruments, which operate without separate return electrodes, can deliver electrical signals to a focused tissue area with reduced risks.

Even with the relatively focused surgical effects of bipolar electrosurgical instruments, however, surgical outcomes are often highly dependent on surgeon skill. Enhanced generators have been made to reduce this dependency.

SUMMARY

In accordance with various embodiments, an electrosurgical system for sealing, fusing and/or cutting tissue is provided. The electrosurgical system may include an electrosurgical generator and an electrosurgical instrument or device. The electrosurgical generator, according to the embodiments of the present invention, may include a digital closed-loop control system that regulates the delivery of electrosurgical or radiofrequency (RF) energy, adjusts the RF energy and in various embodiments measures and monitors electrical properties, e.g., phase, current, voltage and power, of the supplied RF energy to the connectable electrosurgical instrument. In various embodiments, the digital control system enhances accuracy while ensuring stability in the measurements and regulation of the voltage, current and power of the RF output. This provides the optimal RF output for sealing, fusing and/or cutting tissue/vessels under dynamic conditions, such as for example, variable loads, procedural or operational conditions.

In accordance with one aspect of the present invention, a digital closed-loop control system for use with an electrosurgical generator that supplies electrosurgical RF energy to a surgical site is provided. The digital closed-loop control system may include a feedback system monitoring continually electrical properties of the supplied RF energy and generating digital RF signals relating thereto and a microcontroller configured with a variable gain factor to regulate and control an RF amplifier that generates the supplied RF energy across a plurality of RF regulation modes to provide optimal RF output for surgical procedures under any surgical, operational or procedural conditions.

In accordance with a second aspect of the present invention, a method for dynamically controlling an electrosurgical generator that supplies electrosurgical RF energy to a surgical site through an electrosurgical instrument is provided. The method includes the steps of retrieving desired RF setpoints or target values for a plurality of RF regulation modes and generating RF energy at the desired RF setpoints; measuring electrical characteristics of RF output via at least one channel from a feedback system and communicating real and imaginary components of measured data to a microcontroller. The microcontroller, after receiving the transmitted data, performs power calculations to obtain magnitudes of measured data and tissue impedance load for each of the plurality of RF regulation modes.

The method further includes the steps of generating an error signal across the plurality of RF regulation modes and selecting one regulation mode based on the calculated error values; calculating a variable gain factor for each of the plurality of regulation modes using specific algorithms and selecting one variable gain factor based on calculated error values; determining output control signals for Buck and H-Bridge circuitry of an RF amplifier of the electrosurgical generator; and controlling an amount of RF output of the electrosurgical generator in response to the output control signals to maintain a desired output value of the generator.

In accordance with a third aspect of the present invention, there is provided an electrosurgical system for performing surgical procedures. The electrosurgical system may include an electrosurgical generator adapted to supply RF energy to a surgical site and an electrosurgical instrument connected to the electrosurgical generator. The electrosurgical instrument having at least one active electrode adapted to apply electrosurgical RF energy to tissue at the surgical site. The electrosurgical generator may include a primary FPGA (fully programmable gate array) which is configured to cause: generating error signals across a plurality of RF regulation modes and selecting one regulation mode; computing a variable gain factor for the plurality of regulation modes and selecting one variable gain factor; generating an integral signal by integrating the selected error signal and multiplying the generated integral signal by the selected variable gain factor; and driving duty cycles for Buck and H-Bridge circuitry of the RF amplifier using respectively a predicted output voltage and the generated integral signal.

In accordance with a fourth aspect of the present invention, an electrosurgical generator is provided. The electrosurgical generator may include an RF amplifier for supplying RF energy, a feedback system adapted to continually monitor electrical properties of supplied RF energy to generate digital RF signals relating thereto and a primary microcontroller programmed to compute a variable gain factor and a preload function that allows for dynamically controlling the supplied RF energy across a plurality of RF regulation modes and a plurality of RF resolution settings under any surgical, operational or procedural conditions.

In accordance with a fifth aspect of the present invention, a method for impedance evaluation of an electrosurgical instrument, connected to an electrosurgical generator, prior to performing surgical procedures is provided. The method includes the steps of initiating a low voltage mode or passive mode upon activation of the connected electrosurgical instrument; generating RF output limited to values defined by the low voltage mode; measuring electrical characteristics of the RF output and transmitting digitally the measured data to a microcontroller of the electrosurgical generator; calculating other electrical characteristics of the RF output based on the received measured data and transmitting the calculated results to a primary processor within the microcontroller; and determining whether the calculated results has met a certain criteria set by a device script of the connected electrosurgical instrument.

In accordance with a sixth aspect of the present invention, there is provided an electrosurgical generator that includes an RF amplifier for supplying RF energy and a microcontroller configured to dynamically control the supplied RF energy across at least one regulation mode from a plurality of RF regulation modes and a plurality of RF resolution settings.

In accordance with a seventh aspect of the present invention, there is provided an electrosurgical generator that includes an RF amplifier for supplying RF energy and a microcontroller configured to determine at least one of a variable gain factor and a preload function to dynamically control the supplied RF energy.

Many of the attendant features of the present inventions will be more readily appreciated as the same becomes better understood by reference to the foregoing and following description and considered in connection with the accompanying drawings.

BRIEF DESCRIPTION OF THE DRAWING

The present disclosure is described in conjunction with the appended figures.

Figure 1:
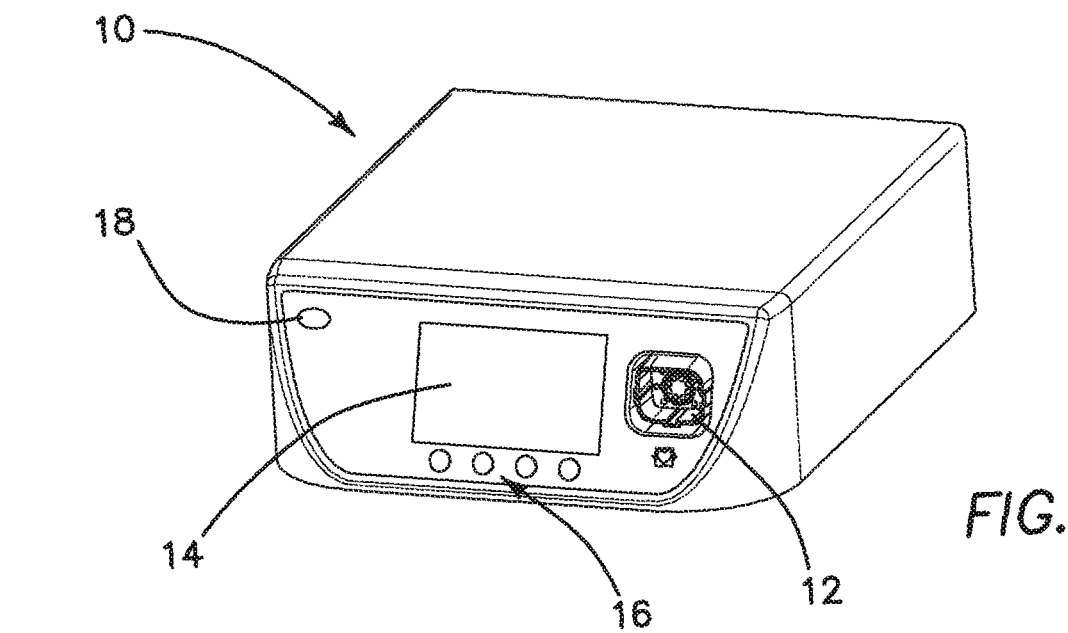
FIG. 1 is a perspective view of an electrosurgical generator in accordance with various embodiments of the present invention.

In the appended figures, similar components and/or features may have the same reference label. Where the reference label is used in the specification, the description is applicable to any one of the similar components having the same reference label.

DETAILED DESCRIPTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiments of the disclosure. It should be understood that various changes may be made in the function and arrangement of elements without departing from the spirit and scope of the invention as set forth in the appended claims.

This disclosure relates in general to electrosurgical systems. It specifically relates to a new generation of electrosurgical generators capable of regulating voltage, current and power of the RF output under dynamically changing impedance loads and control conditions.

Embodiments of the present invention are directed to systems and methods for enhancing surgical outcomes by providing generators having optimal RF output for sealing, fusing and/or cutting tissue or vessels under all dynamic conditions such as, for example, varying tissue impedance load due to electrosurgical operations or tissue affects and any operational conditions and commands determined by the surgeon, surgical procedure and/or device script. This is achieved by implementing a digital closed-loop control system to regulate voltage, current, and power of the RF output. The digital closed-loop control system may include an RF amplifier for generating RF energy, a feedback system for constantly measuring and monitoring the electrical characteristics, e.g., voltage, current, and power, of the supplied RF energy to a connectable electrosurgical instrument and a microcontroller for processing measurement data from the feedback system and adjusting the output of the RF amplifier to meet a desired regulation target under any varying conditions.

According to the embodiments of the present invention, the feedback system measures, via at least one channel, analog RF output and digitizes the measurements. The feedback system in various embodiments collects its voltage and current measurements simultaneously from the RF amplifier and digitizes the measurements through analog to digital converters (ADC). The feedback system is configured to process the digitized values, to derive real and imaginary components of the voltage and current RF output, and to supply the real and imaginary components to the primary microcontroller.

In accordance with the embodiments of the present invention, the primary microcontroller, calculates individual error values for voltage, current and power and based on the individual error values selects a regulation mode. The primary microcontroller in various embodiments calculates, using specific algorithms, a specific variable gain factor for each regulation mode that allows the electrosurgical system according to the embodiments of the present invention to have a critically damped step response under any variable conditions, e.g., surgical, operational or procedural.

In the following, the electrosurgical system and method according to the present invention is explained in detail with sections individually describing: the electrosurgical generator, the electrosurgical instrument and the digital closed-loop control system and method used according to the embodiments of the present invention for providing optimal RF output under any dynamically outside changing conditions.

In accordance with various embodiments, an electrosurgical generator is provided that controls the delivery of electrosurgical or radiofrequency (RF) energy, adjusts the RF energy and in various embodiments measures and monitors electrical properties, e.g., phase, current, voltage and power, of the supplied RF energy to a connectable electrosurgical instrument to ensure optimal sealing, fusing and/or cutting of tissues or vessels. In various embodiments, the generator may include a feedback system that determines such electrical properties and through a microcontroller regulates and/or controls an RF amplifier that generates the required RF energy to provide the optimal RF output for sealing, fusing and/or cutting tissue or vessels under dynamic conditions, such as for example, varying loads, procedural or operational conditions.

Figure 2:
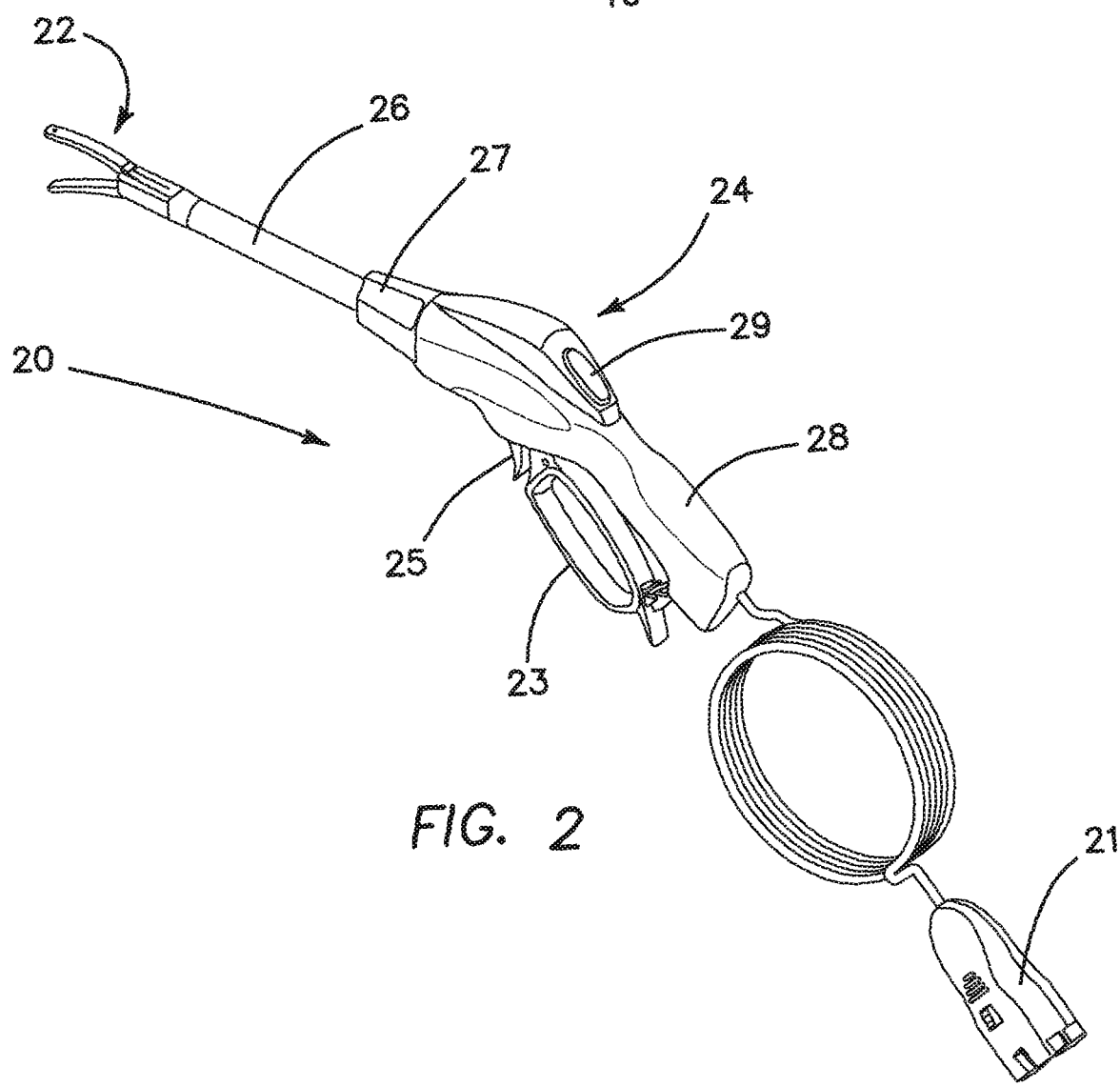
FIG. 2 is a perspective view of an electrosurgical hand device in accordance with various embodiments of the present invention.

Referring first to FIGS. 1-2, an exemplary embodiment of an electrosurgical system for use in surgical procedure is illustrated. As shown in these figures, the electrosurgical system may include an electrosurgical generator 10 and a removably connectable electrosurgical tool or instrument 20. The electrosurgical hand device or instrument 20 can be electrically coupled to the generator 10 via a cabled connection with a device key or connector 21 extending from the instrument 20 to a device connector or access port 12 on the generator 10. The electrosurgical instrument 20 may include audio, tactile and/or visual indicators to apprise a user of a particular or predetermined status of the instrument 20 such as, for example, a start and/or end of a fusion operation. In some embodiments, a manual controller such as a hand or foot switch can be connectable to the generator 10 and/or instrument 20 to allow predetermined selective control of the instrument such as to commence a fusion operation.

In accordance with various embodiments, the electrosurgical generator 10 includes a display 14 that may indicate the status of the electrosurgical system including, among other information, the status of the one or more electrosurgical instruments and/or accessories, connectors or connections thereto, the state or operations of the generator and error indicators. The electrosurgical generator 10 in accordance with various embodiments of the present invention may include a user interface such as, for example, a plurality of buttons 16. The plurality of buttons 16 allows for user interaction with the electrosurgical generator 10. This user interaction may include, for example, requesting an increase or decrease in the electrical energy supplied to one or more instruments 20 that are coupled to the electrosurgical generator 10. In various embodiments, the generator 10 further includes a user-accessible power-on switch or button 18 that when activated powers the generator 10 and activates or initiates a self-verification system test of the generator. In other embodiments, the display 14 can be a touch screen display thus integrating data display and user interface functionalities.

In various embodiments, the electrosurgical generator 10 of the present invention is configured to output radiofrequency (RF) energy through the connectable electrosurgical instrument or hand device 20 to seal, fuse and/or cut tissue or vessels via one or more electrodes. The electrosurgical generator 10, according to the embodiments of the present invention, is configured to generate up to 300V, 8 A, and 375 VA of RF energy and it is also configured to determine a phase angle or difference between RF output voltage and RF output current of the generator during activation or supply of RF energy. In this way, the electrosurgical generator 10 regulates voltage, current and/or power and monitors RF energy output (e.g., voltage, current, power and/or phase). In one embodiment, the generator 10 may stop, terminate or otherwise disrupt RF energy output under predetermined conditions. By way of example, these predetermined conditions may be any of the following conditions: when a device switch is de-asserted (e.g., fuse button released), a time value is met, and/or active phase angle and/or change of phase is greater than or equal to a phase and/or change of phase stop value indicating end of an operation such as fusion or cutting of tissue.

The electrosurgical instrument 20, according to the embodiments of the present invention, may include an elongate shaft 26 having a proximal end coupled to or from which an actuator 24 extends and a distal end coupled to or from which jaws 22 extend. A longitudinal axis extending from the proximal end to the distal end of the elongate shaft 26. In one embodiment, the actuator 24 may include a movable handle 23 which is pivotably coupled to a stationary handle or housing 28. The movable handle 23 is coupled to the stationary handle or housing 28 through a central or main floating pivot. In operation, the movable handle 23 is manipulated by a user, e.g., a surgeon, to actuate the jaws 22 at the distal end of the elongate shaft 26, and thereby, selectively opening and closing the jaws 22. When tissue or vessels are grasped between the jaws 22, a switch or button 29 is activated by the surgeon to seal, fuse and/or cut the tissue/vessels between the jaws 22. Once the button 29 is activated, associated circuitry or contacts are connected to connect appropriate electrodes of the jaws with associated connections of the generator 10 to supply RF energy to tissue grasped between the jaws 22 or otherwise in contact with the one or more electrodes of the jaws.

In various embodiments, the electrosurgical instrument 20 further includes a mechanical or electrical cutting blade that can be coupled to a blade actuator such as a blade lever or trigger 25 of the stationary handle or housing 28. The cutting blade is actuated by the blade trigger 25 to divide or cut the tissue between the jaws 22. In various embodiments, a blade slider is connected to the blade trigger 25 and a protrusion extends from a proximal portion of the blade slider into an opening in one end of the blade trigger connecting the components together. The other end of the blade trigger is exposed and accessible by the user with the blade trigger 25 being pivotable about a trigger pivot at or near the mid-point of the blade trigger. As such, as the blade trigger 25 is pulled or rotated by the user proximally, the end of the blade trigger connected to the blade slider slides or moves the blade slider distally. Integrated with or attached to a distal end of the blade slider is a cutting blade, knife or cutting edge or surface. As such, as the blade slider translates longitudinally through a blade channel in the jaws, tissue grasped between the jaws 22 is cut. In one embodiment, the cutting edge or surface is angled to facilitate cutting of the tissue between the jaws 22. In various embodiments, the cutting blade is a curved blade, a hook, a knife, or other cutting element that is sized and configured to cut tissue between the jaws 22.

Figure 3:
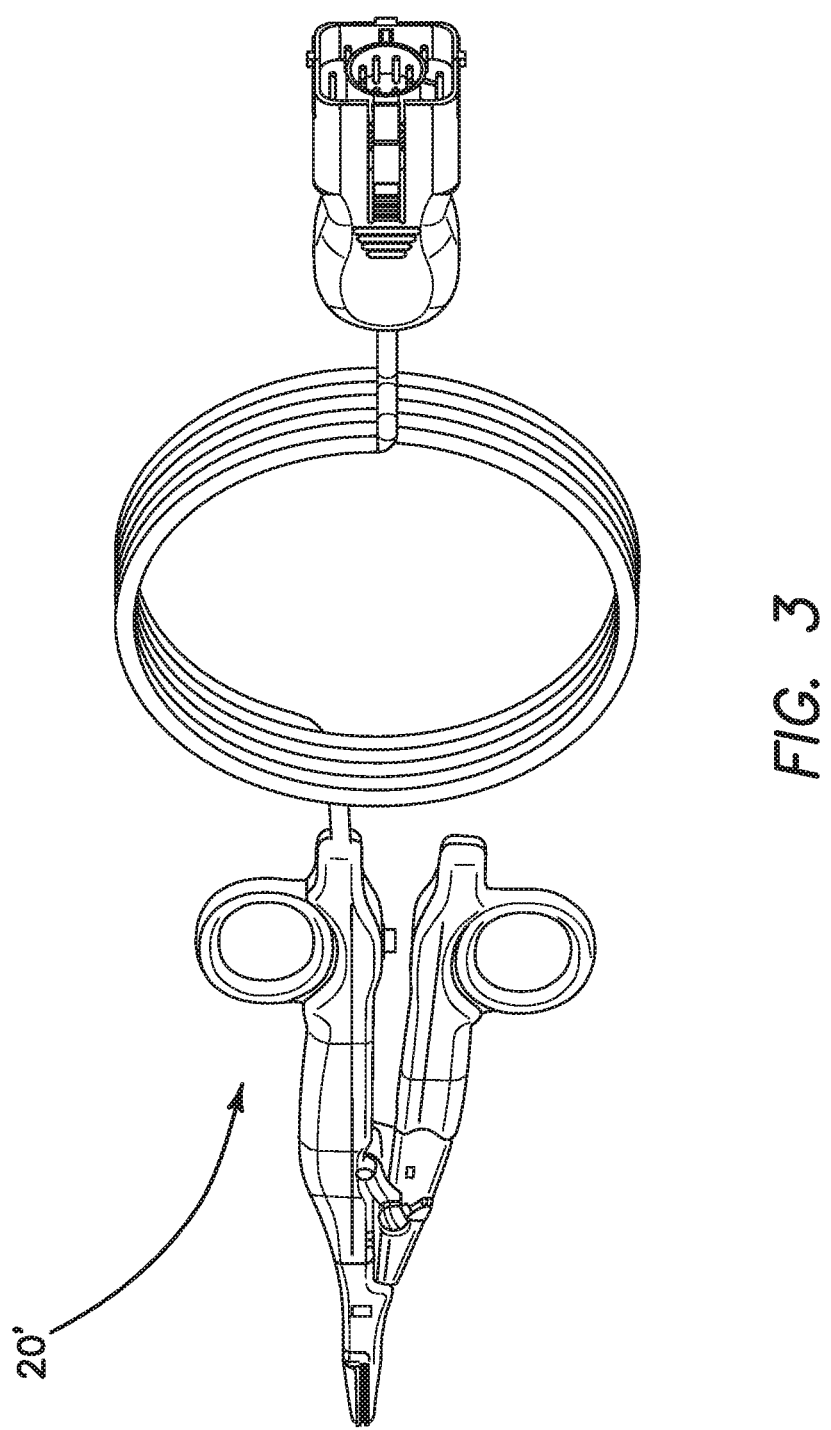
FIG. 3 is a perspective view of an alternative embodiment of an electrosurgical hand device in accordance with various embodiments of the present invention.

In accordance with various embodiments, the elongate shaft 26 comprises an actuation tube or rod coupling the jaws 22 with the actuator. In one embodiment, the actuator includes a rotation shaft assembly including a rotation knob 27 which is disposed on an outer cover tube of the elongate shaft 26. The rotation knob 27 allows a surgeon to rotate the shaft of the device while gripping the actuator. In various embodiments, the elongate shaft 26 is rotatable 360 degrees and in other embodiments, rotation of the elongate shaft 26 is limited to 180 degrees, i.e., ninety degrees clockwise and ninety degrees counter clockwise. FIG. 3 illustrates an alternative embodiment of an electrosurgical hand device 20' connectable to the electrosurgical generator 10. The electrosurgical hand device 20' is similar but includes different features and has a different surgical use than the electrosurgical hand device 20.

Figure 4:
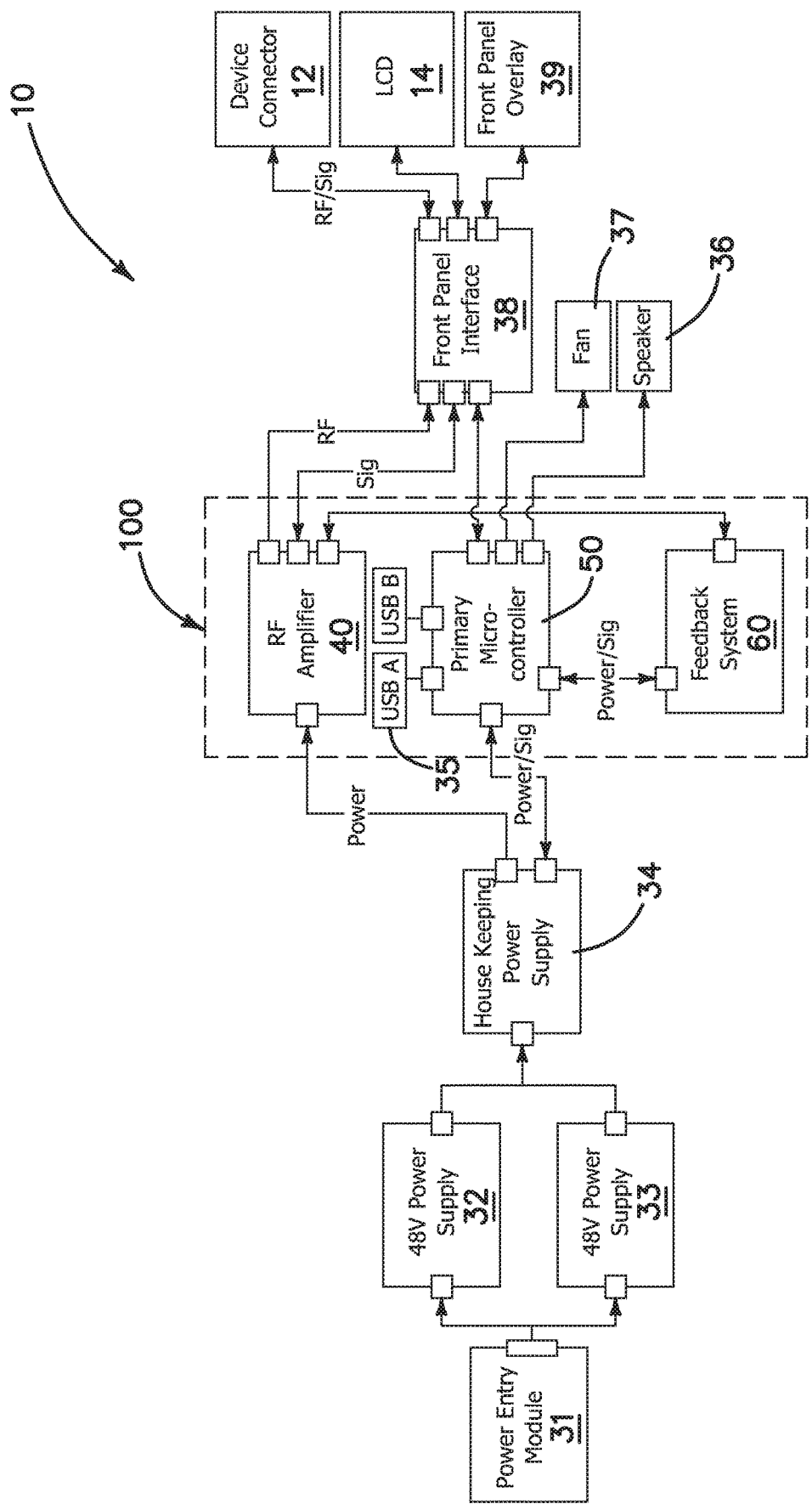
FIG. 4 depicts a block diagram of an electrosurgical generator in accordance with various embodiments of the present invention.

Referring next to FIG. 4, a block diagram of an electrosurgical generator 10 according to the embodiments of the present invention is shown. As shown in this figure, the electrosurgical generator 10 may include a power entry module 31, e.g., an AC main input, coupled to a power supply module, e.g., two 48V DC power supplies 32, 33. The power supply module converts the AC voltage from the AC main input to a DC voltage and via a house keeping power supply 34 provides power to various circuitry of the generator 10 and in particular supplies power to an RF amplifier 40 that generates or outputs the RF energy. In one embodiment, the RF amplifier 40 may include a Buck and H-Bridge circuitry to convert a DC voltage input into an RF output and in another embodiment into a variable amplitude 350 kHz sine wave. The DC voltage input is a 96V DC input that is generated by the two 48V DC power supplies 32, 33 coupled in series. One of the 48V DC power supply 32, 33 is configured to generate low voltage rails and in particular supply standby voltage to power on the generator 10.

According to the embodiments of the present invention, the electrosurgical generator 10 further includes a control system or a digital integral servo control system 100 to regulate and control the RF output. As shown in FIG. 4, the control system 100 may include the RF Amplifier 40, a primary microcontroller 50 and a feedback system 60. The RF output and in various embodiments the amplitude of the RF waveform output is controlled and regulated by the electrosurgical control system 100 which is embedded or integrated within the electrosurgical generator 10. The control system 100 varies between regulating voltage, current, or power of the RF output generated by the RF Amplifier 40. In various embodiments, the feedback system 60 measures the RF output and, after processing the measured data, digitally feeds the RF output's real and imaginary components to the primary microcontroller 50. The primary microcontroller 50, according to the embodiments of the present invention, processes the received data from the feedback system 60 and adjusts the output of the RF amplifier 40 to meet a desired regulation target. In various embodiments, the feedback system 60 comprises of analog input, digital processing and digital output.

In various embodiments, the electrosurgical generator 10 logs all RF output data onto an internal memory device, e.g., a secure digital (SD) or non-volatile memory card. The memory device is configured to be read through an interface port 35, e.g., a universal serial bus (USB) port, on the electrosurgical generator 10. In various embodiments, the generator 10 is configured to copy the data from the internal memory device to a connectable portable storage device, e.g., a USB flash drive, through the interface port of the generator.

In accordance with various embodiments of the present invention, the electrosurgical generator 10 is further configured to provide RF output in three resolution settings or modes: low voltage, normal or medium voltage and high voltage ranges. In various embodiments, device scripts stored and located on connectable electrosurgical hand devices, e.g., instrument 20, and/or connectors coupled thereto, e.g., device key 21, are used to determine or set the RF output or voltage mode.

Referring back to FIGS. 1 & 4 and in accordance with various embodiments, the electrosurgical generator 10 is configured to alert the surgeon when the vessel has reached a completed procedure state, e.g., a completed seal state, or if an error or fault condition has occurred. The electrosurgical generator 10 in various embodiments may include visual, tactile and/or audible outputs to provide such alerts or other indicators or information to the surgeon as dictated by the surgical procedure, device script or health or operational information regarding the device 20 and/or generator 10. In one embodiment, the generator 10 via a front panel interface 38 alerts the surgeon through the LCD display 14, which is integrated into a front panel of the generator, and in various embodiments provides specific audible alarm or informational tones through a speaker 36 also integrated into the front panel of the generator. The generator 10 in various embodiments may include a front panel overlay 39 that provides a user interface or access including navigational push buttons to allow user access to systems settings such as volume or display brightness. The front panel overlay 39 may also include the system power button or connection. In various embodiments, a fan system 37 is provided to assist in heat dissipation. Additionally, as illustrated in the FIG. 4, signal or sig represents connections that, for example, comprise of digital signals used to communicate information across systems and/or printed circuit boards, power represents connections that, for example, comprise of voltage rails used to power systems and/or printed circuit boards and RF represents connections that, for example, comprise of high voltage, high current RF energy used to seal, fuse or cut tissue or vessels.

Figure 5:
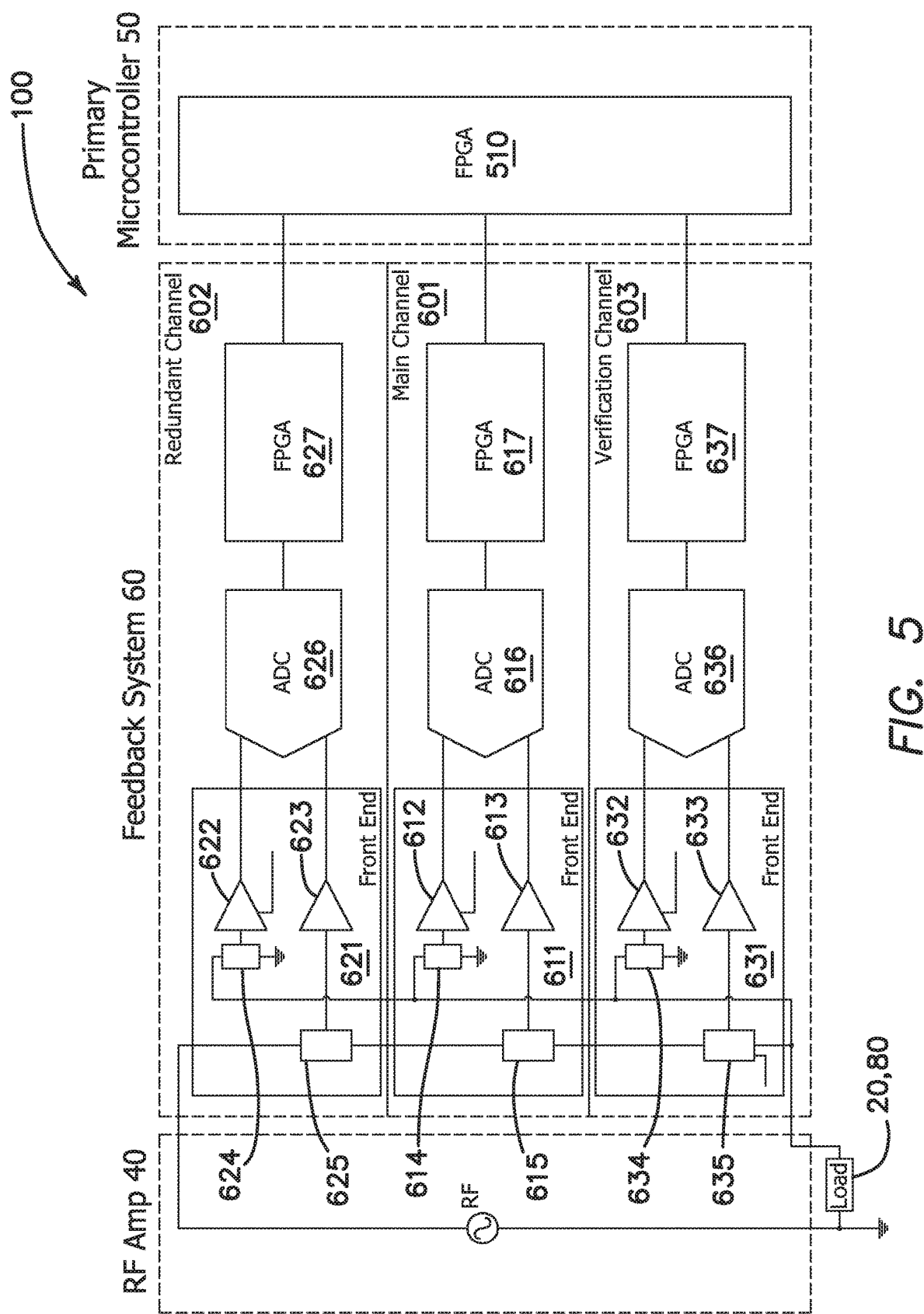
FIG. 5 depicts, in greater detail, a block diagram of an embodiment of a feedback system within a control system of an electrosurgical generator.

FIG. 5 illustrates, in greater detail, a block diagram of an embodiment of a feedback system 60 within the control system 100 of an electrosurgical generator 10. As described further above and also shown in FIG. 5, the control system 100 may include the RF Amplifier 40, the primary microcontroller 50 and the feedback system 60. In accordance with various embodiments of the present invention, the RF amplifier 40 generates an RF output and the feedback system 60 measures various electrical properties of the RF signal outputted from RF amplifier 40. According to the embodiments of the present invention, the verification system 60 may include a main channel 601, a redundant channel 602 and a verification channel 603. The main channel 601 and redundant channel 602 in various embodiments may include separate but identical components. Additionally, the main and redundant channels 601 and 602 follow separate but identical electrical paths and in one embodiment are both connected to the RF amplifier 40 and the RF output.

Similarly, components of the verification channel 603 are separate from the main and redundant channels 601 and 602 but are similar. In one embodiment, the verification channel 603 may include the same components as the main and redundant channels 601 and 602, but the components in the verification channel 603 have higher ratings, e.g., higher resolution and/or lower drift, and are often more costly. In another embodiment, the verification channel 603 may include the same components as the main and redundant channels 601 and 602. The verification channel 603 also follows a separate but identical electrical path as the main and redundant channels 601 and 602 and in one embodiment is connected to the RF amplifier 40 and the RF output. In various embodiments, the feedback system 60 measures analog RF output and digitizes the measurements. The feedback system 60 is configured to measure and digitize the RF output via at least one channel, e.g., main channel 601. In this embodiment, the feedback system 60 through the main channel 601 measures the analog RF output via a front end circuitry 611.

As shown in FIG. 5, the front end circuitry 611 may include a shunt resistor 615 coupled to a pre-amplifier 613 to measure the current of the RF output. In various embodiments, the front end circuitry 611 further includes a voltage divider 614 coupled to a pre-amplifier 612 to measure the voltage of the RF output. Outputs of the pre-amplifiers 612, 613 are supplied to an analog to digital converter (ADC) 616, thereby digitizing the current and voltage measurements. The digitized values are further processed to derive real and imaginary components of the voltage and current RF output. In various embodiments, the digitized values from the ADC 616 are supplied to a fully programmable gate array (FPGA) 617 of the feedback system 60. The FPGA 617 is configured for processing the digitized voltage and current measurements values to generate real and imaginary components of the voltage and current RF output using a discrete Fourier transform. The digital real and imaginary components are then supplied to the primary microcontroller 50 and, in one embodiment, via a serial communication protocol.

Figure 6:
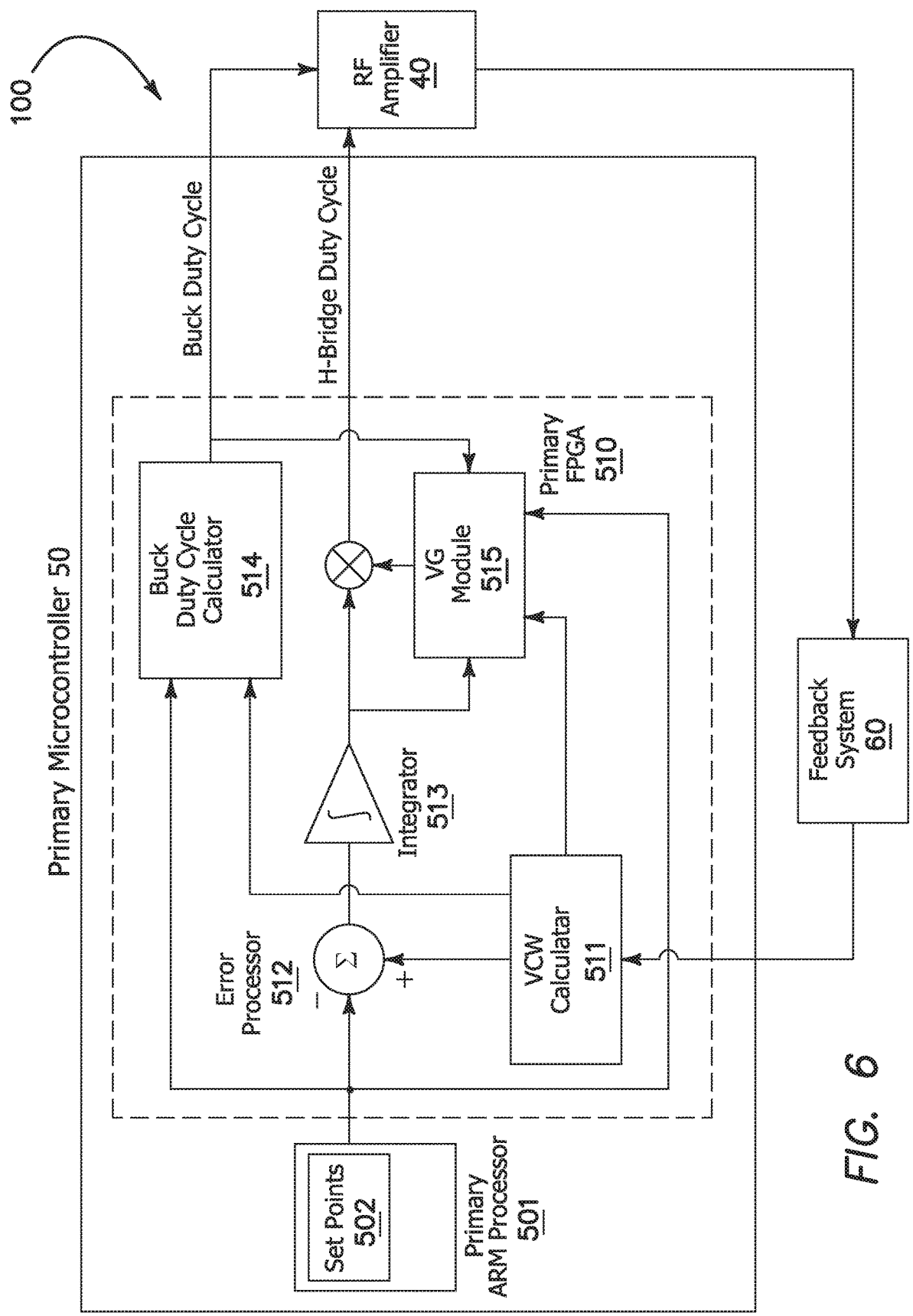
FIG. 6 depicts, in greater detail, a block diagram of an embodiment of a primary microcontroller within a control system of an electrosurgical generator.

With reference to FIG. 6, a schematic illustration of an embodiment of a control system 100 depicting, in greater detail, a block diagram of an embodiment of a primary microcontroller 50 of an electrosurgical generator 10 is shown. As shown in this figure, the primary microcontroller 50 may include a primary ARM (advanced reduced instruction set machine) processor 501 and a primary FPGA (fully programmable gate array) 510. The primary ARM processor 501 is configured to establish desired output values, such as for example, voltage, current and/or power as setpoints 502. In various embodiments, the desired output values may be provided by a device script. In accordance with various embodiments, the primary FPGA 510 of the primary microcontroller 50 receives the digital real and imaginary components of the voltage and current measurements and calculates the magnitudes of the voltage, current and power of the RF output. The magnitude of the voltage, current and power of the RF output is calculated using a VCW (voltage, current, power) calculator 511, as shown in FIG. 6. Individual error values for voltage, current and power are also calculated by an error processor 512. In one embodiment, error values are calculated by subtracting a desired voltage, current and power setpoints from the measured magnitudes.

The error processor 512 calculates the relative error between the main channel measurements and the setpoints values 502, and based on the error values determines or selects a regulation mode. Accordingly, the error processor 512 determines which of the three regulation modes, e.g., voltage, current and power, should be reinforced or activated by the electrosurgical generator 10. In various embodiments, the calculated error values for the selected mode is integrated by an integrator 513 to generate an error signal that is directly proportional to and is used to correct the output of the RF amplifier 40.

According to the embodiments of the present invention, the calculated error values may also be used to determine a variable gain factor for each regulation modes, e.g., voltage, current and power, of the generator 10. The variable gain is configured to use a different predefined set of calculations or algorithm based on the selected regulation mode. As shown in FIG. 6, a VG (variable gain) module 515 is used to compute the variable gain value ($K_i$) for each regulation modes, e.g., voltage, current and power. The variable gain factor, according to the embodiments of the present invention, may be computed as a function of the voltage, current and power setpoints, the calculated outside impedance load or tissue load, the Buck voltage value as well as the value of the error integral or any combination thereof. As such, the variable gain in various embodiments provides critical step responses for all setpoints and impedance load conditions or any changes thereto. In other words, the variable gain according to the embodiments of the present invention allows for the electrosurgical generator 10 to be critically damped under any varying conditions such as, for example, surgical, operational and procedural conditions. In various embodiments, the variable gain factor may be recalculated on a predetermined schedule or timing such as, for example, every period of the RF output.

In accordance with various embodiments and with further reference to FIG. 6, the primary microcontroller 50 is configured to predict the necessary output voltage of the generator 10 to regulate the RF amplifier 40. In various embodiments, the primary FPGA 510 of the primary microcontroller 50 may use the calculated impedance loads and the voltage, current and power setpoints to predict the necessary voltage of the generator 10. The predicted value is then used by a Buck Duty Cycle calculator 514 to calculate a duty cycle value for a pulse width modulator (PWM) of an integrated Buck circuit of the RF amplifier 40. On the other hand, the product of the error integral and the calculated variable gain factor for the selected mode ($K_i * \int e(t)$) may be used to derive a duty cycle value for an H-Bridge circuit of the RF amplifier 40. As such, the control system 100 according to the embodiments of the present invention is capable of providing dynamic regulation of the variable or varying RF output of the generator 10. In various embodiments, the electrosurgical generator 10 may be switching between voltage, current and power regulation modes. In such embodiments, the control system 100 is configured to perform a preload calculation or preload function, the details of which will be discussed further down below, to provide a gradual, non-disruptive transition in the RF output.

The control system 100, according to the embodiments of the present invention, provides regulation of RF output under dynamically changing impedance loads, e.g., due to electrosurgical operations or electrosurgical tissues affects, and control conditions, e.g., device scripts or user operations. The control system 100 being configured with a variable gain rather than a fixed gain allows the control system 100 to adjust for different load impedances and output voltages and thus not be limited to be optimized, e.g., for the lowest load impedance and/or highest output voltage. The control system 100 is also configured to account for the system becoming over damped as impedance increases that can result in non-optimal phase margin and dynamic or unpredictable behavior and thus affect the ability of the control system 100 to track or follow dynamic commands, e.g., device script operations. The control system 100 of the generator ensures that tissue electrosurgical effects, such as for example, sealing, fusing or cutting, are optimized through critical responses of the control system to dynamically changing tissue impedance conditions and operational conditions and commands determined by the surgeon, surgical procedure and/or device script.

As described further above, the feedback system 60 according to the embodiments of the present invention may include a second channel, e.g., the redundant channel 602, which is nearly identical to the main channel 601. The measurements from the redundant channel 602 and the resulting calculations are being constantly compared to the measurements and calculations of the main channel 601 to verify the operation of the main channel 601. As such, if the main and redundant channels 601 and 602 have differing measurements or calculations, then a generator error is recognized and the supply of RF energy halted.

In accordance with various embodiments, the feedback system 60 may include various other systems and circuitry, e.g., a sampler or other calculator (not shown in the figures), to provide sampling and/or other calculations as required by the electrosurgical control system 100 of the present invention. In various embodiments, the feedback system 60 measures analog voltage and current of the RF output of the RF amplifier 40 and in various embodiments the feedback system 60 takes a predetermined number of samples per each RF output cycle operating at 350 KHz for each measurement of voltage and current. In some embodiments, the feedback system 60 may utilize demodulations and transforms to obtain zero frequency components or filtering out unwanted higher order frequency harmonics out of the measured voltage and current values. As described further above, the feedback system 60 communicates or transmits, e.g., serially, the measured real and imaginary voltage and current values to the primary microcontroller 50.

In what follows, operational modes and functional blocks of various circuitry and systems within the primary FPGA 510 will be explained in detail with sections individually describing: the VCW calculator 511, the error processor 512, the integrator 513, the Buck Duty Cycle calculator 514 and the VG module 515.

Figure 7:
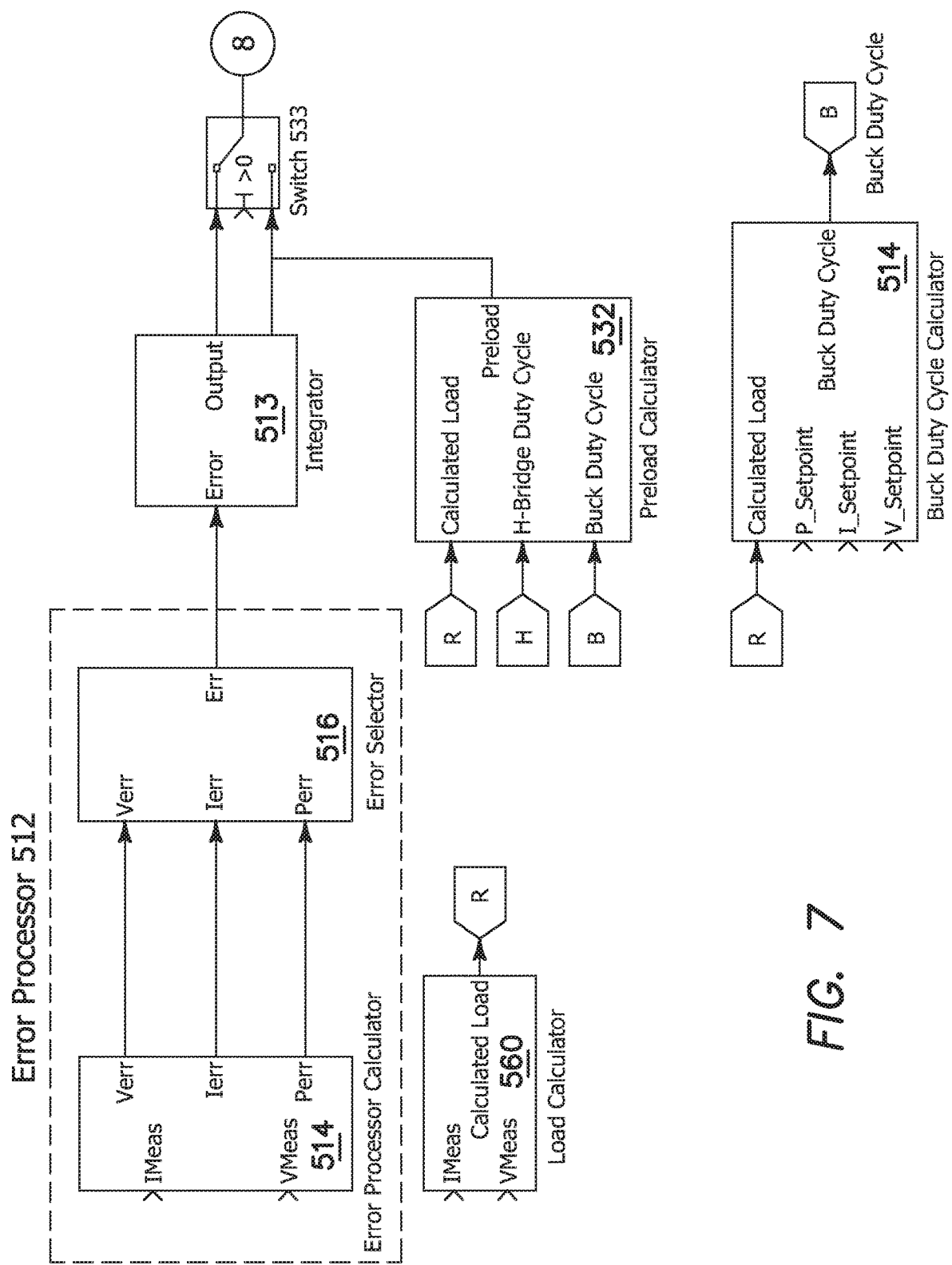
FIGS. 7-8 is a schematic illustration of operational modes and functional blocks of various circuitry and systems within a primary microcontroller of an electrosurgical control system of the present invention.
Figure 8:
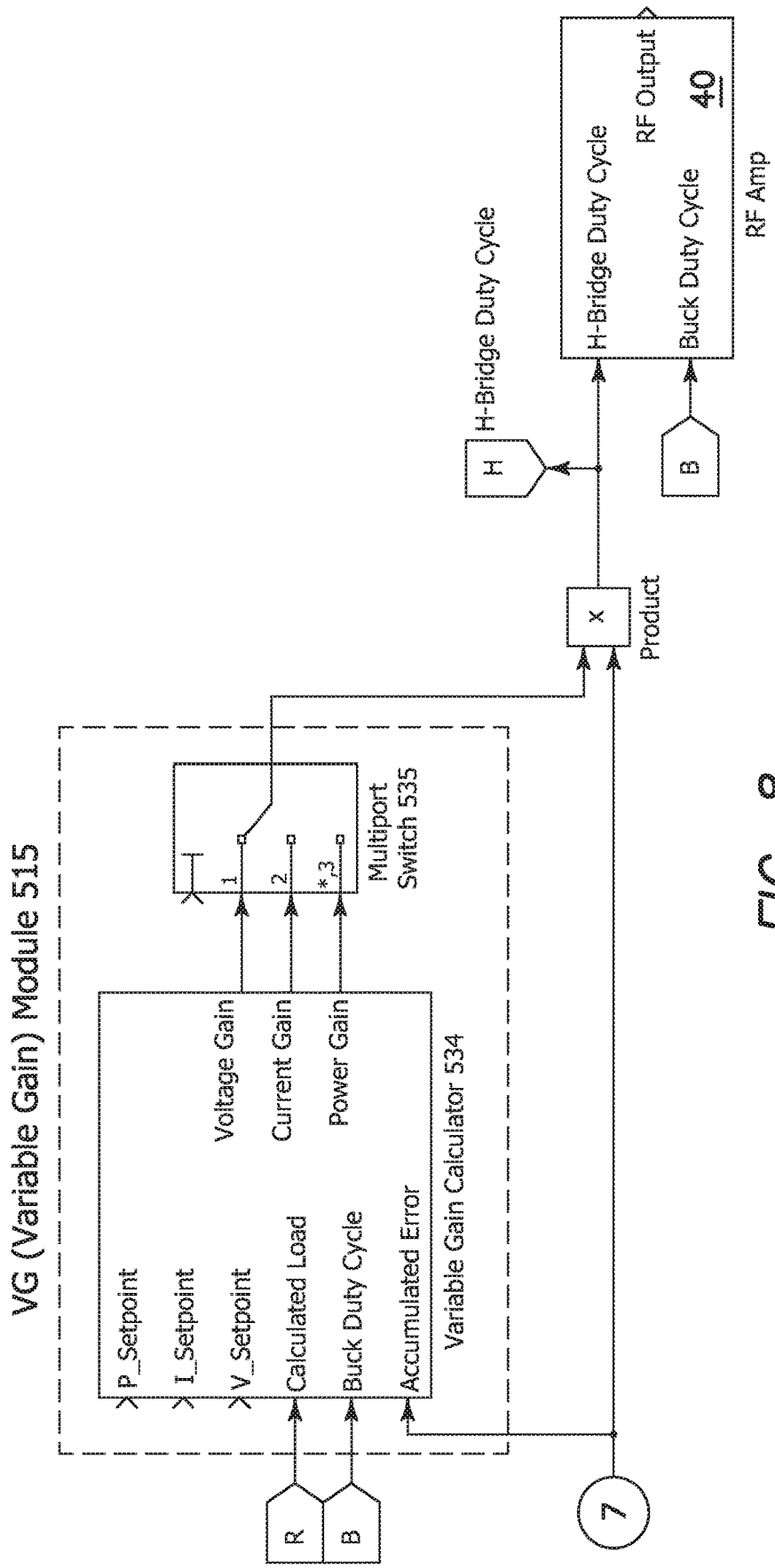

FIGS. 7-8 is a schematic illustration of operational modes and functional blocks of various circuitry and systems within a primary microcontroller 50 of an electrosurgical control system 100 of the present invention. According to the embodiments of the present invention, the primary FPGA 510 receives the measured real and imaginary voltage and current components or values from the feedback system 60 and uses these components to calculate their respective root means square (RMS) magnitudes using the VCW calculator 511. The VCW calculator 511 may further include a load calculator 560 (best shown in FIG. 7). The load calculator 560 uses the feedback system voltage and current measurement values to calculate the impedance load or tissue load. In some embodiments, filtered voltage and current measurement values are used for calculating the impedance load.

The primary FPGA 510 is further configured to perform error processing using the error processor 512. As shown in FIG. 7, the error processor 512 may include an error calculator 514 and an error selector 516. The error processor 512 calculates the error between the main channel measurements from the feedback system 60 and the setpoints values and determines which regulation mode is required for the correction of the RF output power. This is achieved by calculating the relative error between the setpoints and the measurements and in various embodiments this error calculation is performed simultaneously on voltage, current, and power by the error calculator 514. The error processor 512 utilizes the error selector 516 for determining which regulation mode needs to be enforced by the electrosurgical generator 10. Accordingly, the error selector 516 will select the regulation mode based on the most positive calculated error value. As such, the error with the most positive value will dictate which regulation mode is to be used by the electrosurgical generator 10. The primary FPGA 510 in various embodiments also normalizes the calculated magnitudes with respect to its maximum count value and then converted to floating point values.

The integrator 513 is constantly integrating the error with the most positive value, e.g., selected regulation mode. In operation, since the RF amplifier 40 may be switching between different RF regulation modes, e.g., voltage, current and power regulation modes, the integrator 513 needs to be preloaded with another value that allows the RF output to stay constant while transitioning between various regulation modes. For this purpose, a preload function or preload calculator 532 is implemented within the primary FPGA 510 (best shown in FIG. 7). The preload function or calculator 532 is configured to calculate the variable gain for the mode to which the RF amplifier is transitioning to and preload this value into the integrator 513 using a relay or switch 533 (best shown in FIG. 7). The preload function is calculated using the counts for the Buck and H-Bridge circuitry of the RF amplifier and the calculated tissue impedance load. This ensures a seamless transition between various regulation modes.

The primary FPGA 510 provides a variable integral control system to dictate the output for the Buck and H-Bridge (best shown in FIG. 8) controls of the RF amplifier 40. In various embodiments, variables used by the variable integral control system may include, for example, impedance load or tissue load calculations, setpoints for voltage current and power as well as the calculated RMS magnitude for the voltage, current, and power. The load calculator 560 may use filtered voltage and current measurement values for calculating the impedance or tissue load. In some embodiments, the variable integral control system only directly regulates voltage and in order to regulate current or power, a corresponding voltage value must be calculated. In various embodiments, the Buck duty cycle calculator 514 (best shown in FIG. 7) uses the calculated impedance load and the setpoints for voltage, current and power to predict where the output voltage of the RF amplifier 40 should be. The predicted voltage value is then used to generate the counts for the integrated Buck PWM circuit of the RF amplifier 40. The output voltage of the Buck PWM circuits of the RF Amplifier 40 sets the main voltage rails of the integrated H-Bridge PWM circuit of the RF amplifier 40.

According to the embodiments of the present invention, using the prediction set forth by the variable integral control system, the primary FPGA 510 sets counts for the Buck PWM circuit of the RF amplifier 40 and in various embodiments responds quickly to reach roughly close to the desired output value, e.g., the predicted voltage value. In various embodiments, the primary FPGA 510 drives PWM signals to the Buck and H-Bridge (best shown in FIG. 8) configurations or circuitry of the RF amplifier 40. In various embodiments, the determination of the PWM signals for the H-Bridge configurations is used to fine tune the RF output to the desired output. The duty cycle for the H-Bridge circuit of the RF amplifier 40 is defined by the multiplication of the calculated variable gain factor and an integral signal or error integral for the selected mode (best shown in FIG. 8). As can be seen in FIG. 8, the VG (variable gain) module 515 may include a variable gain calculator 534 and a multiport selector 535. The variable gain calculator 534 calculates the variable gain for each regulation mode, e.g., voltage, current and power, and selects the appropriate variable gain factor based on the same criteria that was used by the error processor 512, e.g. the error with the most positive value. The calculated variable gain may be defined as a function of the calculated impedance load, voltage, current and power setpoints, the Buck voltage value and the integral error or accumulated error. In various embodiments, the primary FPGA 510 converts respective numerical duty cycle counts to drive the PWM signals that controls the Buck and H-Bridge configurations.

In various embodiments, the primary ARM processor 501 verifies the validity of the setpoints and ensures the setpoints for voltage, current, and power meet the threshold for the mode the electrosurgical generator 10 is operating in. In accordance with various embodiments, calibration values are stored in an EEPROM of the feedback system 60. These values are specific predefined coefficients used to eliminate discrepancies or tolerances on the feedback system 60. In various embodiments, all three channels 601, 602 and 603 have calibration values for voltage, current, and power for normal or medium, high, and low voltage modes with the exception of the verification channel 603 not having a low voltage mode. The modes as such dictates the correct calibration coefficients for voltage, current, and power being used in the servo calculations. This also is based on the regulation mode the generator is operating in.

In various embodiments, the error processor 512 further includes one or more constants, such as a normalization factor, error coefficient and/or point positions (useful for floating point conversions). In various embodiment, the primary microcontroller 50 calculates the error between the main channel measurements and the setpoint values to determine which regulation mode to be used for the correction of the servo, e.g., the output of the RF energy. In various embodiments, the primary microcontroller 50 uses the calculated measurements and the error processor coefficient to obtain an absolute measurement. With this absolute measurement, the primary microcontroller 50 uses the calibration coefficient to obtain a calibrated absolute measurement and with the normalization factor obtains a relative measurement. The primary microcontroller compares the difference between the relative measurement and the setpoint established by the primary processor 501 to determine the relative error.

In accordance with various embodiments, the primary microcontroller 50 using multiplexers provide the respective values of the relative error to be calculated for voltage, current and power and comparisons are performed between the calculated errors to output the greatest or largest positive error to determine the regulation mode for the generator.

Using the selected regulation mode and its corresponding voltage value, the primary microcontroller 50 calculates the voltage output needed for optimal operation of the generator 10. In various embodiments, as the control system 100 adjusts the output voltage, current and power output targets are translated into their respective voltages at calculated loads. The regulation mode then decides which calculated output will be used in the control system 100.

In various embodiments, the control system 100 operates as a variable integral control loop. Variables are the voltage, current and power measurements, setpoints, and load calculations and the system operates at a predefined frequency, e.g., 350 KHz frequency, with the ability to switch between integral control loops. The electrosurgical generator 10 as such provides a control system for voltage, current and power driving sources and thus provides a generator integral control loops for current, voltage and power. Additionally, since switching between the integral control loops occurs when regulation modes are changed, the control system 100 implants the preload function for each mode, i.e., voltage, current and power, to ensure a smooth transition between the regulation modes.

In accordance with various embodiments, the feedback system 60 may include three channels: the main channel 601, the redundant channel 602 and verification channel 603. The main and redundant channels 601 and 602 are largely identical while the verification channel 603 has similar functionalities to the main and redundant channels 601 and 602, but has higher resolution, lower tolerance, and lower drift components.

In accordance with various embodiments, each of the channels 601, 602 and 603 of the feedback system 60 may include an analog portion that attenuates and amplifies the RF voltage/current measurement signals. In various embodiments, RF voltage signals are attenuated by a network of resistor dividers before being differentially amplified to drive the ADCs (616, 626, 636). In various embodiments, all three channels 601, 602 and 603 have different sets of amplifier gain resistors to measure different voltage modes, i.e., a normal voltage mode and a high voltage mode. In various embodiments, the normal voltage mode includes voltages less than or equal to 166V and in high voltage mode, voltages less than or equal to 322V. In accordance with various embodiments, the main and redundant channels 601 and 602 have an alternative set of resistor configuration to more accurately measure lower voltages and in various embodiments voltages less than or equal to 10V. The verification channel's resistor dividers in various embodiments contain much lower tolerance and lower drift resistors than that of the main and redundant channels 601 and 602.

In accordance with various embodiments, the RF current measurement signal is taken across a shunt resistor (615, 625, 635) from each channel of the verification system 60. All shunt resistors 615, 625, and 635 in various embodiments are in series, so each channel measures the same current signal. The main and redundant channels 601 and 602 in various embodiments have an alternative set of shunt resistors to more accurately measure lower currents, e.g., currents less than or equal to 100 mA. The verification channel 603 has shunt resistors that are lower tolerance and lower drift than that of the main and redundant channels 601 and 602.

In accordance with various embodiments, the measured signals after the amplifiers (612, 613; 622, 623; 632, 633) are passed through filters for ADC input filtering. The verification channel 603 has filter components with much lower tolerance and lower drift than that of the main and redundant channels 601 and 602. In various embodiments, the filter of the verification channel has a steeper rolloff and thus has a steeper attenuation of higher frequencies.

In accordance with various embodiments, data conversion components are independent between each of the three channels 601, 602 and 603. The ADCs (616, 626, 636) convert the analog voltage and current measurement signals to discrete samples that are processed by the respective channel's FPGAs (617, 627, 637). The verification channel's ADC 636 has more resolution, e.g., more bits, and has lower drift than that of the main and redundant channels 601 and 602. In various embodiments, the verification channel's ADC 636 also has a local generated reference voltage to accurately set the input range of the ADC 636.

In various embodiments, the feedback system's FPGAs (617, 627, 637) performs I/Q demodulation on the discrete voltage and current measurement samples to obtain real and imaginary samples. The measured values are passed through a discrete Fourier transform to obtain the DC component of the real and imaginary values for the voltage and current measurements. In various embodiments, the verification channel 603 contains a locally generated digital voltage rail to accurately power its FPGA's I/O pins.

In accordance with various embodiments, each channel of the feedback system 60 independently communicates its data to the primary microcontroller 50 through independent communication connections. In various embodiments, the verification channel's data is only used by a self-verification system or process at predefined time or schedule, e.g., at the start-up of the generator 10. During the self-verification process, the verification channel's data is compared with the main and redundant channel's data to verify the accuracy and functionalities of the main and redundant channels 601 and 602. In various embodiments, throughout RF related operations, the main channel's data is the only set of data used by the control system 100 and the redundant channel's data is constantly compared with the main channel's data to ensure the main channel 601 is operating within predefined parameters and/or tolerances.

According to the embodiments of the present invention, the servo control system 100 of the electrosurgical generator 10 may include the RF amplifier 40, the feedback system 60 and the primary microcontroller 50. The feedback system 60 creates a path for a closed-loop system between the RF amplifier 40 and the primary microcontroller 50. The feedback system 60 in various embodiments measures the voltage and current of the supplied RF signals and calculates the real and imaginary components of the measurements within one or more channels 601, 602 and 603. In one embodiment, only one channel is provided for the feedback system 60, the main channel 601. In another embodiment, two channels are provided, the main and redundant channels 601 and 602. In yet another embodiment, three channels are provided, the main channel 601, the redundant channel 602 and the verification channel 603. The calculated components within the one or more channels are transmitted or communicated to the primary microcontroller 50.

In accordance with various embodiments, the main and redundant channels 601 and 602 are copies of one another and are used by the primary microcontroller 50 to monitor the voltage and current of the RF output during operation of the electrosurgical generator 10. The verification channel 603 is similar to the other two channels 601 and 602, but includes components, for example, that are more drift resistant and/or uses ADCs with higher resolutions. This channel, in various embodiments, is used on startup of the generator, where self-verification of the generator is performed. The feedback system 60 in various embodiments collects its voltage and current measurements simultaneously from the RF amplifier 40. In various embodiments, the generated RF signal produces a voltage across one or more internal loads, e.g., load 80 (best shown in FIG. 5), disposed inside the RF amplifier 40 or a tissue load, e.g., electrosurgical hand device 20, 20'. The feedback system 60 in various embodiments collects current being delivered by using its own shunt resistors (615, 625, 635) and measures the voltage across them. To measure voltage, the feedback system 60 provides three voltage dividers (614, 624, 634) which are parallel to the load 20, 80. All measurements in various embodiments are converted to their real and imaginary components by the FPGAs 617, 627, and 637. The real and imaginary components are sent to the primary microcontroller 50 causing the feedback system 60 to act as a feedback device between the primary microcontroller 50 and the RF amplifier 40.

In accordance with various embodiments, the feedback system 60 measures the analog RF output via front end circuitry 611, 621, 631. Front end circuitry may include shunts 615, 625, 635 coupled to respective pre-amplifiers 613, 623, 633 to measure the current of the RF output. In various embodiments, the front end circuitry may also include voltage dividers 614, 624, 634 coupled to respective pre-amplifiers 612, 622, 632 to measure the voltage of the RF output. Outputs of the pre-amplifiers are supplied to respective analog to digital converters (ADCs) 616, 626, 636 thereby digitizing the current and voltage measurements. The digitized values are processed to derive real and imaginary components of the voltage and current RF output. In various embodiments, the digitized values from respective analog to digital converters (ADC) are supplied to FPGAs 617, 627, 637.

In various embodiments, the electrosurgical generator 10 is configured to provide RF output in a low voltage mode during a passive impedance evaluation which is automatically set by the generator 10. According to the embodiments of the present invention, the electrosurgical generator 10 is automatically set to the low voltage mode prior to execution of any device script. The device script in various embodiments represents a procedural walkthrough of a surgical operation that may include the application and termination of RF energy to the tissue. During a medium or normal voltage mode, the electrosurgical generator 10 according to the embodiments of the present invention is configured for having an output RF energy up to 150V or 8 A and is mainly used in tissue sealing. During a high voltage mode, the electrosurgical generator 10 according to the embodiments of the present invention is configured for having an output RF energy up to 300V or 4 A and is mainly used in tissue cutting. During the low voltage mode, the electrosurgical generator 10 according to the embodiments of the present invention is configured for having an output RF energy up to 10V and 100 mA and is mainly used in passive tissue impedance evaluations and measurements at a level that does not create a physiological response in tissue.

In accordance with various embodiments, specific device scripts are stored on specific electrosurgical hand devices 20, 20' that are optimized for a specific surgical procedure to produce consistent electrosurgical sealing and/or cutting of tissue. In various embodiments, RF output parameters or settings are defined in the device scripts and used by the electrosurgical generator 10 to regulate or control the RF output for the specific surgical procedure and/or electrosurgical hand device 20, 20'. The device script and associated RF output parameters in various embodiments are retrieved or transferred to the generator 10 when the electrosurgical hand device 20, 20' is connected to the generator 10. In one embodiment, the primary ARM processor 501 may retrieve the device script from a memory storage attached to or integrated into the device key 21 that connects the electrosurgical device 20, 20' to the electrosurgical generator 10.

Figure 9:
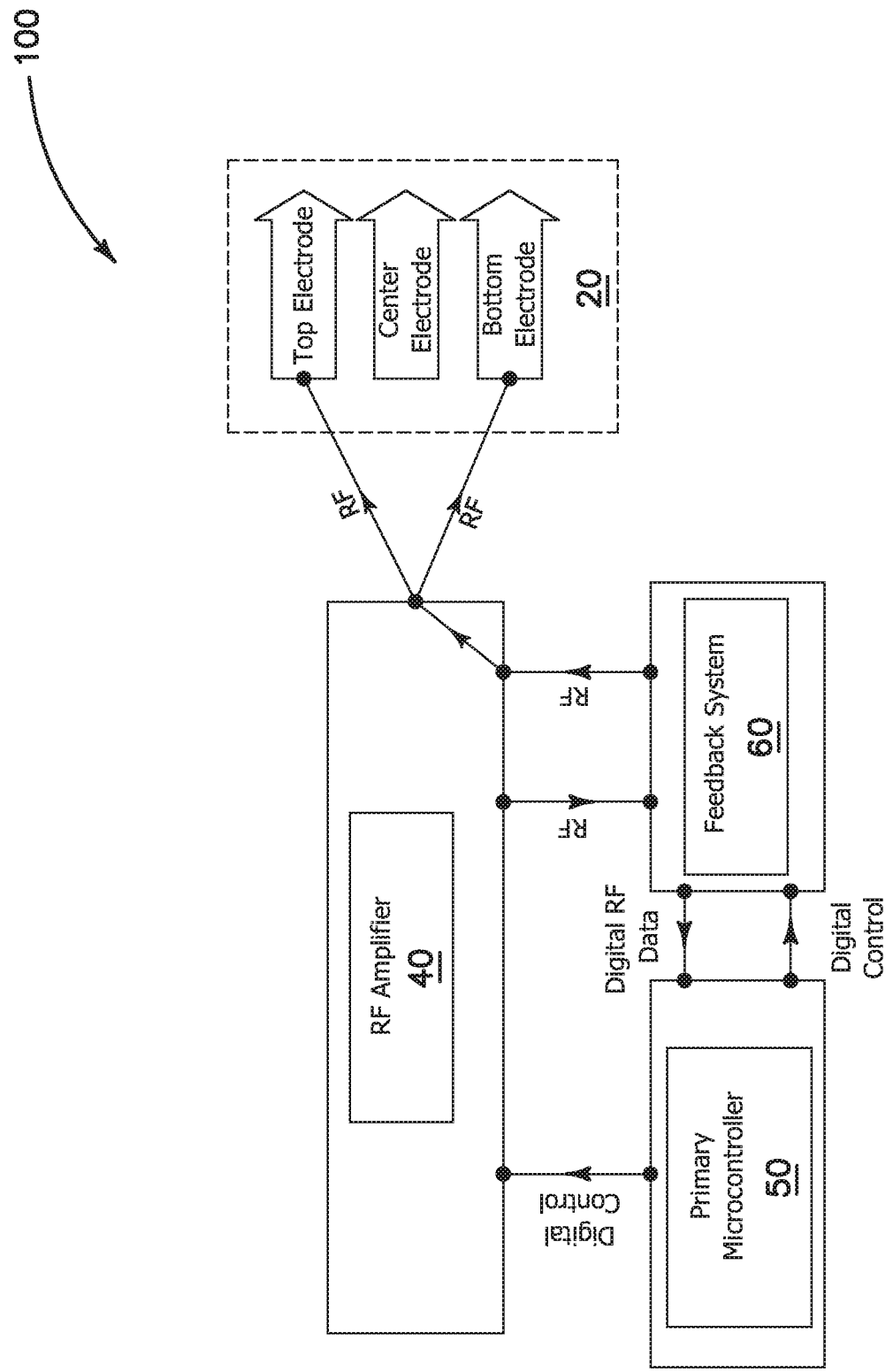
FIG. 9 depicts a block diagram of an embodiment a control system of an electrosurgical generator operating in a passive regulation mode.

Referring next to FIG. 9, a block diagram of an embodiment a control system 100 of an electrosurgical generator 10 operating in a passive regulation mode is shown. In accordance with various embodiments of the present invention, the electrosurgical generator 10 is configured to provide a passive measurement regulation mode or low voltage mode to verify whether a connected electrosurgical hand device 20, 20' can be used for specific surgical procedures such as, for example, sealing, fusing and/or cutting tissues or vessels. Thus, the passive regulation mode is triggered at a predetermined time, e.g., at each activation of the connected electrosurgical hand device 20, 20'. The passive mode is configured to detect open and/or short loads in the RF output path. In one embodiment, an open or short condition is predetermined and in various embodiments, is an acceptable impedance range or value defined by a device script included with the connected electrosurgical hand device 20, 20' or otherwise associated with such electrosurgical hand devices 20, 20'. In various embodiments, the RF output for the passive mode has a lower static limit than other RF regulation modes and is used for a limited duration before normal RF regulation or operations of the electrosurgical generator 10 start. The low level RF output in various embodiments does not create a physiological response in tissue.

In various embodiments, when the electrosurgical generator 10 is operating in the passive mode, the RF amplifier 40 supplies a 350 KHz RF output via relays to the connected electrosurgical instrument 20, 20'. As described further above, the RF output in the low voltage mode or passive mode is limited to not more than 10V rms and/or not more than 100 mA rms. The control system 100 regulates and measures voltage and current via the feedback system 60. The primary microcontroller 50 determines if a short and/or open condition is encountered based on the device script and the measured voltage and current data from the control system 100. In various embodiments, one or more electrodes (best shown in FIG. 9) are used in passive mode and position or selection of the electrodes, e.g., top, center or bottom, may vary based on the connected electrosurgical device, e.g., device 20, 20' and/or the position of the electrodes relative to the subject tissue or vessel.

In accordance with various embodiments, when a surgeon asserts a fuse or cut switch, the electrosurgical control system 100 initiates a passive impedance evaluation. The passive impedance evaluation triggers or identifies a fault, if a short or open condition is detected at the jaws 22 or distal working end of the electrosurgical hand device 20, 20'. If the passive impedance check is successful, the primary ARM processor 501 executes the full device script. In various embodiments, the primary ARM processor 501 instructs other circuitry of the electrosurgical generator 10 to output RF energy based on specific conditions, triggers, events and timing and according to specific settings. In various embodiments, the primary ARM processor 501 ensures the electrosurgical device is supplied specific RF energy according to specific output settings (voltage, current and power set points) and varies the RF output through the course of the procedure or surgical operation depending on various triggers defined by the device script.

Figure 10:
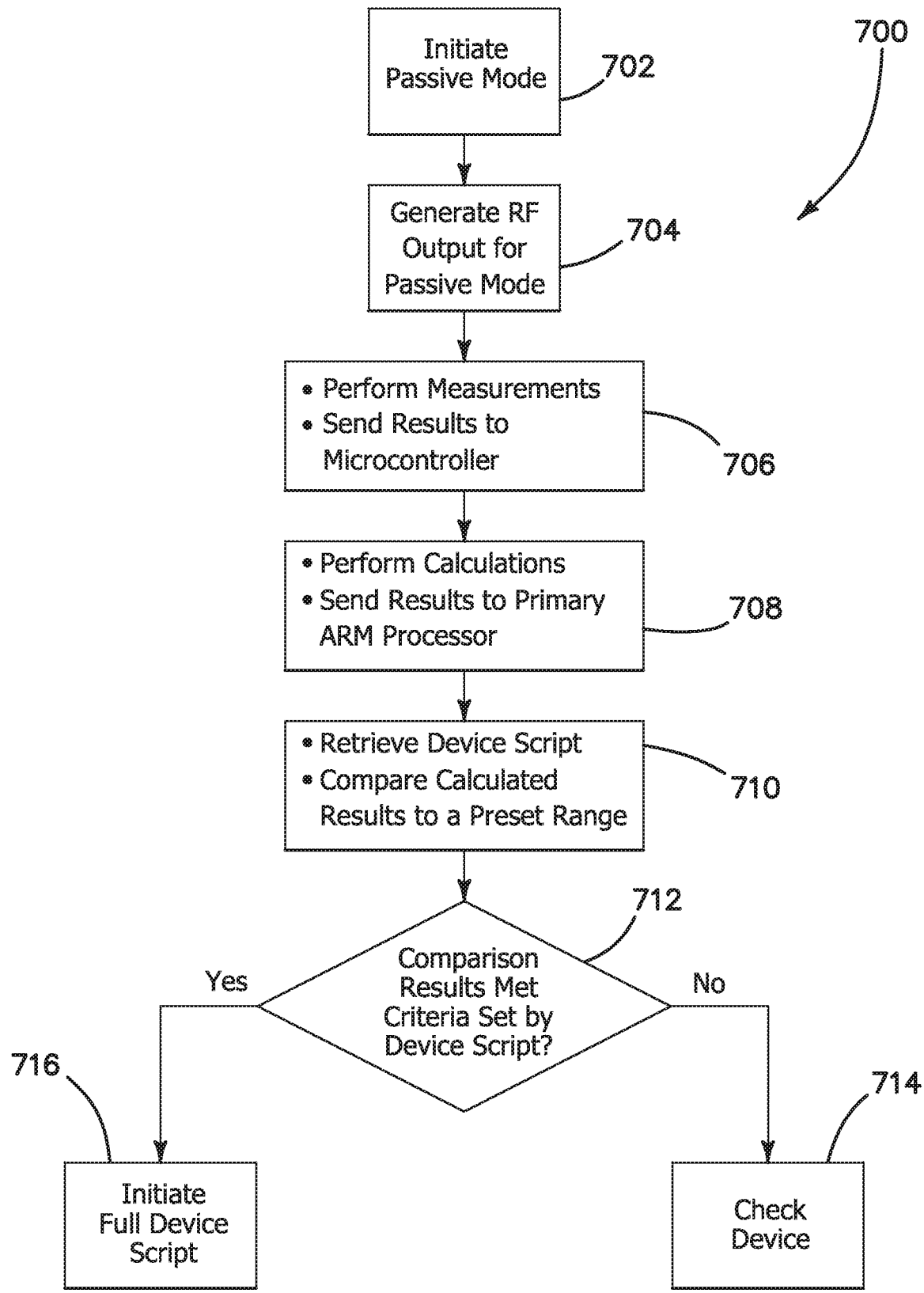
FIG. 10 illustrates a flow diagram of an embodiment of a passive regulation mode operations or process of an electrosurgical generator according to the embodiments of the present invention.

FIG. 10 illustrates a flow diagram of an embodiment of a passive regulation mode operations or process according to the embodiment of the present invention. The depicted portion of the process 700 begins in step 702 where the algorithm initiates the passive mode as a starting point. In accordance with various embodiments, the passive mode is initiated or triggered at each activation of the connected electrosurgical hand device 20, 20' by a surgeon or other users. After initiating the passive mode, the processing goes to block 704 for generating RF output in the low voltage mode or passive mode and supplying RF energy to the connected electrosurgical hand device 20, 20'. In various embodiments, when the electrosurgical generator 10 operates in the passive mode or low voltage mode, the RF signal outputted from the RF amplifier 40 is limited to a specified voltage range (≤10V) and a specified current range (≤10 mA) for a range of 5-500 ohms resistance.

Once the RF output for the passive mode is generated, processing flows to block 706 where the feedback system 60 measures the electrical characteristics of the RF output. The control system 100, in accordance with various embodiments of the present invention, regulates the RF output to a set value as directed by the passive or low voltage mode and the feedback system 60 measures voltage, current, and/or phase from the main channel 601 and digitally feeds some or all of the measured values to the primary microcontroller 50. After completion of measurements and transmission of measured data, processing flows to block 708 where the primary FPGA 510 calculates or determines other electrical characteristics of the RF output based on the received data or readings and transmits some or all of the calculated results to the ARM processor 501 of the primary microcontroller 50. Other electrical characteristics of the RF output according to the embodiments of the present invention may include tissue impedance load and/or power. Once the calculated results are received by the primary ARM processor 510, the processing flows to block 710 where the primary ARM processor 501 retrieves the device script and compares the calculated results, e.g., calculated impedance load or tissue load, to a preset range set by the device script. In one embodiment, the device script is stored into a memory attached to or integrated into the device key or connector 21 that connects the electrosurgical hand device 20, 20' to the electrosurgical generator 10.

A determination of whether the comparison results has met certain criteria set by the device script is made in step 712. Examples of the certain criteria may include, but not limited to, whether the comparison results or readings are within maximum and/or minimum values set by the device script. If the comparison results or readings are not between maximum and/or minimum values set by the device script, processing flows from block 712 to block 714 where an error is generated to notify the user or surgeon of an error and/or to check the electrosurgical device and/or its position relative to the tissue or vessel. In accordance with various embodiments, to supply RF energy after such a notification, the electrosurgical device 20, 20' must be reactivated and the passive tissue impedance evaluation, e.g., passive mode or low voltage mode, be reinitiated.

If the comparison results or readings are between maximum and/or minimum values set by the device script, processing goes from block 712 to block 716 where the primary ARM processor 501 initiate the full device script to provide optimized RF energy for sealing, fusing and/or cutting tissue or vessel.

As described further above and in accordance with various embodiments, the control system 100 of the electrosurgical generator 10 may include one or more resolution settings and in various embodiments it includes three settings: low, normal or medium and high voltage setting. These resolution settings are different from the regulation modes and in some embodiments they require some adjustments to the circuitry that measures the RF output. Each setting is configured to require different hardware configurations for the feedback system 60 and/or different normalization algorithms in the calculations performed by the primary microcontroller 50. In various embodiments, the voltage measurement circuit of the feedback system 60 uses a different resistor selection or configuration for each of the three settings. In various embodiments, the current measurement circuit of the feedback system 60 uses the same resistor configuration for two of the settings, e.g., normal and high voltage settings, and a different resistor configuration for the low voltage setting.

In one embodiment, while the electrosurgical generator 10 is operating in the passive mode, the operations or process assigned to the primary ARM processor 501 may be performed via an FPGA. In other embodiments, other control systems may be incorporated therein. In yet another embodiment, a proportional, e.g., adjusting the system to reach setpoints, integral, e.g., measuring an area between error values and a time axis, prediction, e.g., predicting future errors based on a current error slope, architecture or any combination thereof may be included to supplement or replace the control system measurements, calculations and/or regulation.

In various embodiments, the electrosurgical generator 10 may supply an RF output having different waveform characteristics, e.g., square, providing non-sinusoidal periodic waveforms alternating between a minimum and maximum value; triangle, providing non-sinusoidal periodic waveforms with asymmetric ramps upward to a maximum value and downward to a minimum value; and/or sawtooth, providing non-sinusoidal waveforms with ramps upward to a maximum value and dropping sharply to a minimum value. In accordance with various embodiments of the present invention, the electrosurgical generator 10 may supply an RF output having different crest factor characteristics such as providing a ratio of peak value to effective value of a waveform, a peak amplitude divided by RMS value, and/or an ideal or perfect sine wave having a crest factor of 1.414.

The above description is provided to enable any person skilled in the art to make and use the electrosurgical devices or systems and perform the methods described herein and sets forth the best modes contemplated by the inventors of carrying out their inventions. Various modifications, however, will remain apparent to those skilled in the art. It is contemplated that these modifications are within the scope of the present disclosure. Different embodiments or aspects of such embodiments may be shown in various figures and described throughout the specification. However, it should be noted that although shown or described separately each embodiment and aspects thereof may be combined with one or more of the other embodiments and aspects thereof unless expressly stated otherwise. It is merely for easing readability of the specification that each combination is not expressly set forth.

Although the present invention has been described in certain specific aspects, many additional modifications and variations would be apparent to those skilled in the art. It is therefore to be understood that the present invention may be practiced otherwise than specifically described, including various changes in the size, shape and materials, without departing from the scope and spirit of the present invention. Thus, embodiments of the present invention should be considered in all respects as illustrative and not restrictive.

What is claimed is:

1. A digital closed-loop control system for use with an electrosurgical generator that supplies electrosurgical RF energy to a surgical site, the digital closed-loop control system comprising:
    a feedback system for continually monitoring electrical properties of the supplied RF energy to the surgical site as a concurrent surgical condition and generating digital RF signals relating thereto; and
    a microcontroller, responsive to the generated digital RF signals from the feedback system, is configured with a variable gain factor to regulate and control an RF amplifier that generates the supplied RF energy across a plurality of RF resolution settings and a plurality of RF regulation modes,
    wherein the microcontroller is further configured to compute the variable gain factor for each of the plurality of RF regulation modes and select one of the computed variable gain factors based on individual error values calculated for each of the plurality of RF regulation modes; the variable gain factor being selected based on a most positive error value.

2. The digital closed-loop control system of claim 1 wherein the plurality of RF resolution settings comprise at least one of a low voltage setting, a medium voltage setting, and a high voltage setting.

3. The digital closed-loop control system of claim 2 wherein for each RF resolution setting, the plurality of RF regulation modes comprise at least one of a voltage regulation mode, a current regulation mode, and a power regulation mode.

4. The digital closed-loop control system of claim 1 wherein the selected variable gain factor allows the electrosurgical generator to have a critically damped step response under any varying surgical, operational or procedural conditions.

5. The digital closed-loop control system of claim 1 wherein the feedback system comprises of analog input, digital processing and digital output.

6. The digital closed-loop control system of claim 1 wherein the feedback system comprises a plurality of channels; the feedback system is configured to measure the electrical properties of the supplied RF energy via at least one of the plurality of channels, to generate data representative of the measured electrical properties, and to digitally transmit the data to the microcontroller.

7. The digital closed-loop control system of claim 6 wherein the microcontroller is configured to receive the data, perform calculations related thereto to obtain measured magnitudes of voltage, current, and power of the supplied RF energy.

8. The digital closed-loop control system of claim 1 wherein the individual error values are calculated by subtracting desired voltage, current and power setpoints from measured magnitudes of voltage, current, and power of the supplied RF energy.

9. The digital closed-loop control system of claim 1 wherein the microcontroller is further configured to select one of the plurality of RF regulation modes based on the calculated individual error values; the RF regulation mode being selected based on the most positive error value.

10. The digital closed-loop control system of claim 1 wherein the microcontroller is further configured with a preload function allowing a seamless transition of the electrosurgical generator between each of the plurality of RF regulation modes.

11. The digital closed-loop control system of claim 1 wherein the microcontroller comprises a primary fully programmable gate array (FPGA) and a primary processor, wherein the primary FPGA is configured to receive and further process the generated digital RF signals from the feedback system and the primary processor is configured to establish desired RF output values for each of the plurality of RF resolution settings and the plurality of RF regulation modes.

12. The digital closed-loop control system of claim 11 wherein the desired RF output values are provided by a device script; the desired RF output values comprising desired voltage, current, and power setpoints.

13. The digital closed-loop control system of claim 2 wherein the low voltage setting comprises an output RF energy up to 10V or 100 mA, the medium voltage setting comprises an RF output energy up to 150V or 8 A, and the high voltage setting comprises an output RF energy up to 300V or 4 A.

14. The digital closed-loop control system of claim 6 wherein each of the plurality of channels of the feedback system comprises: a front-end circuitry for measuring the electrical properties of the supplied RF energy; an analog to digital converter (ADC) for digitizing the measured electrical properties of the supplied RF energy; and a fully programmable gate array FPGA) for deriving the digital RF signals related to the measured electrical properties of the supplied RF energy.

15. A digital closed-loop control system for use with an electrosurgical generator that supplies electrosurgical RF energy to a surgical site, the digital closed-loop control system comprising:
 a feedback system for continually monitoring electrical properties of the supplied RF energy to the surgical site as a concurrent surgical condition and generating digital RF signals relating thereto; and
 a microcontroller, responsive to the generated digital RF signals from the feedback system, is configured with a variable gain factor to regulate and control an RF amplifier that generates the supplied RF energy across a plurality of RF resolution settings and a plurality of RF regulation modes, wherein the microcontroller is further configured to:
 select one of the plurality of RF regulation modes based on individual error values calculated for each of the plurality of RF regulation modes; the RF regulation mode being selected based on a most positive error value, and
 generate an accumulated error value over time, for the selected RF regulation mode, using an integrator module that includes a variable gain calculator.

16. The digital closed-loop control system of claim 15 wherein the accumulated error value over time is calculated by integrating the calculated individual error values for the selected RF regulation mode.

17. The digital closed-loop control system of claim 15 wherein the variable gain calculator is configured to generate the variable gain factor as a function of desired voltage, current and power setpoints, a measured tissue impedance load, measured magnitudes of voltage, current, and power of the supplied RF energy, and the accumulated error value.

18. The digital closed-loop control system of claim 17 wherein the variable gain calculator is configured with a different algorithm to generate the variable gain factor for each of the plurality of RF regulation modes.

19. The digital closed-loop control system of claim 17 wherein the microcontroller is further configured to provide a variable integral control system for dictating RF output of a Buck and H-Bridge circuitry of the RF amplifier.

20. The digital closed-loop control system of claim 19 wherein the microcontroller is further configured to drive a duty cycle value for the Buck circuitry of the RF amplifier using the desired voltage, current and power setpoints and the measured tissue impedance load.

21. The digital closed-loop control system of claim 19 wherein the microcontroller is further configured to drive a duty cycle value for the H-Bridge circuitry of the RF amplifier using the accumulated error value and the variable gain factor.

\* \* \* \* \*